(12) United States Patent
Hettrick et al.

(10) Patent No.: US 8,435,186 B2
(45) Date of Patent: May 7, 2013

(54) QUANTIFYING AUTONOMIC TONE WITH THORACIC IMPEDANCE

(75) Inventors: Douglas A. Hettrick, Andover, MN (US); Donald J. Hefner, St. Paul, MN (US); Shantanu Sarkar, Roseville, MN (US); Todd M. Zielinski, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 333 days.

(21) Appl. No.: 12/696,753

(22) Filed: Jan. 29, 2010

(65) Prior Publication Data

US 2011/0190654 A1 Aug. 4, 2011

(51) Int. Cl.
*A61B 5/00* (2006.01)
(52) U.S. Cl.
USPC .......................................... 600/508; 600/547
(58) Field of Classification Search .................. 600/508, 600/547; 607/6
See application file for complete search history.

(56) References Cited

U.S. PATENT DOCUMENTS

| | | |
|---|---|---|
| 4,374,382 A | 2/1983 | Markowitz |
| 5,117,824 A | 6/1992 | Keimel et al. |
| 5,545,186 A | 8/1996 | Olson et al. |
| 5,755,736 A | 5/1998 | Gillberg et al. |
| 6,752,765 B1 | 6/2004 | Jensen et al. |
| 7,319,899 B2 | 1/2008 | Keizer |
| 2005/0240233 A1 | 10/2005 | Lippert et al. |
| 2008/0091114 A1* | 4/2008 | Min et al. ...................... 600/508 |
| 2008/0281370 A1 | 11/2008 | Lin et al. |
| 2009/0024005 A1 | 1/2009 | Lewicke et al. |
| 2010/0114204 A1* | 5/2010 | Burnes et al. ..................... 607/4 |

FOREIGN PATENT DOCUMENTS

EP 0985429 A2 3/2000

OTHER PUBLICATIONS

Search Report and Written Opinion from corresponding PCT Application Serial No. PCT/US2010/033915 dated Jul. 15, 2010 (9 pages).
Reply to Written Opinion dated Jul. 15, 2010, from international application No. PCT/US2010/033915, filed Nov. 29, 2011, 10 pp.

* cited by examiner

*Primary Examiner* — Max Hindenburg
(74) *Attorney, Agent, or Firm* — Michael C. Soldner

(57) ABSTRACT

The disclosure describes techniques for quantifying the autonomic nervous system (ANS) health of a patient with thoracic impedance measurements. Thoracic impedance may be measured utilizing cardiac electrodes and an implantable medical device housing or other electrodes located on or within the patient. Since greater variability in thoracic impedance may indicate better health of the ANS, monitoring impedance changes in a patient may be used to quantify autonomic tone of the ANS, and ultimately, overall patient health. In some examples, thoracic impedance may be measured in response to a change in patient posture for acute monitoring or at predetermined times over several days, weeks, or months for more chronic monitoring of the patient. An implantable medical device may independently analyze the impedance measurements and transmit an alert to the patient or clinician when impedance changes indicate a change in patient health.

20 Claims, 13 Drawing Sheets

QUANTIFYING AUTONOMIC TONE WITH THORACIC IMPEDANCE

TECHNICAL FIELD

The disclosure relates to medical devices and, more particularly, medical devices that measure physiological conditions.

BACKGROUND

Autonomic nervous system (ANS) activity provides basic physiological responses to many activities of a person. For example, instantaneous autonomically mediated responses such as environmental mechanical stimulus may help to prevent a loss of blood pressure to the upper extremities of the person due to a sudden posture change like rising from a supine position. This physiological response is achieved by peripheral vasoconstriction of the lower extremities modulated by the ANS. Decreased function of the ANS can lead to undesirable symptoms and ailments, such as loss of consciousness upon a sudden posture change. In addition, decreased ANS function is associated with a significantly worse prognosis for heart failure patients.

ANS activity, or autonomic tone, further influences sinoatrial (SA) node and atrioventricular (AV) node function. An increase in sympathetic tone can result in an increased heart rate and an increased rate of AV nodal conduction. Conversely, an increase in parasympathetic tone can result in decreased heart rate and an increase in AV nodal conduction time. Due to these heart-related indications of autonomic tone, heart rate and heart rate variability are two diagnostic tools commonly used to obtain information about the state of the ANS. Indeed, decreases in heart rate variability, as well as increases in night heart rate, are known to be associated with an increasing incidence of heart failure. Implantable medical devices, therefore, have been used to measure heart rate and heart rate variability for providing indices of autonomic tone to a clinician.

SUMMARY

In general, the disclosure describes techniques for quantifying the autonomic nervous system (ANS) health of a patient with thoracic impedance measurements. Although heart rate and heart rate variability can be used to determine the ANS health, or autonomic tone, of the patient, the heart rate information is only clinically relevant when the heart rate is being controlled by the activity of the SA node. Thus, heart rate information is unavailable as an indication of autonomic tone if, for example the patient is experiencing an atrial tachyarrhythmia, or if the heart rate is controlled artificially by pacing, e.g., atrial pacing. In some patients, these circumstances can occur for a majority, if not all, of a patient's time. Measuring thoracic impedance allows for autonomic tone monitoring regardless of the patient's cardiac health and during periods of artificial pacing.

Thoracic impedance measurements may refer to, as examples, intrathoracic or transthoracic impedance measurements. Thoracic impedance may be measured between cardiac electrodes and an implantable medical device housing, as one example of intrathoracic impedance measurement, or between any combination of electrodes located on or within the patient's thoracic cavity. The impedance may be measured periodically over several days, weeks, or months for chronic ANS monitoring, in response to a change in patient posture or activity, or some other physiological change, for acute monitoring, or in any other type of monitoring method appropriate for the patient's condition.

Greater variability in thoracic impedance over time may indicate greater autonomic tone and better health of the ANS. Therefore, any changes to this impedance variability can be used to quantify the relative autonomic tone of the patient and indicate to the clinician if heart failure is more or less probable. As examples, the changes in impedance can be measured between day and night impedance, over time in response to various posture changes or the same posture change, or the general impedance variability over time. An implantable medical device may independently analyze these impedance measurements and transmit an alert to the patient or clinician when impedance changes indicate a change in patient health. Alternatively, the implantable medical device may merely transmit stored impedance measurements to an external computing device for clinician analysis and review.

In one example, the disclosure provides a method that includes measuring a plurality of thoracic impedance values of a patient, and generating a value of at least one autonomic parameter based on variation of the plurality of measured thoracic impedance values, the autonomic parameter value indicative of a relative autonomic nervous system (ANS) health of the patient.

In another example, a system comprises a plurality of electrodes, a sensing module that measures a plurality of thoracic impedance values of a patient via the electrodes, and a processor that generates a value of at least one autonomic parameter based on variation of the plurality of measured thoracic impedance values, the autonomic parameter value indicative of a relative autonomic nervous system (ANS) health of the patient.

In another example, a system comprises means for measuring a plurality of thoracic impedance values of a patient, and means for generating a value of at least one autonomic parameter based on variation of the plurality of measured thoracic impedance values, the autonomic parameter value indicative of a relative autonomic nervous system (ANS) health of the patient.

In another example, a computer-readable storage medium comprises instruction that cause a processor to measure a plurality of thoracic impedance values of a patient, and generate a value of at least one autonomic parameter based on the measured thoracic impedance values, the autonomic parameter value indicative of a relative autonomic nervous system (ANS) health of the patient.

The details of one or more examples are set forth in the accompanying drawings and the description below. Other features, objects, and advantages of the disclosure will be apparent from the description and drawings, and from the claims.

DETAILED DESCRIPTION

Figure 1:
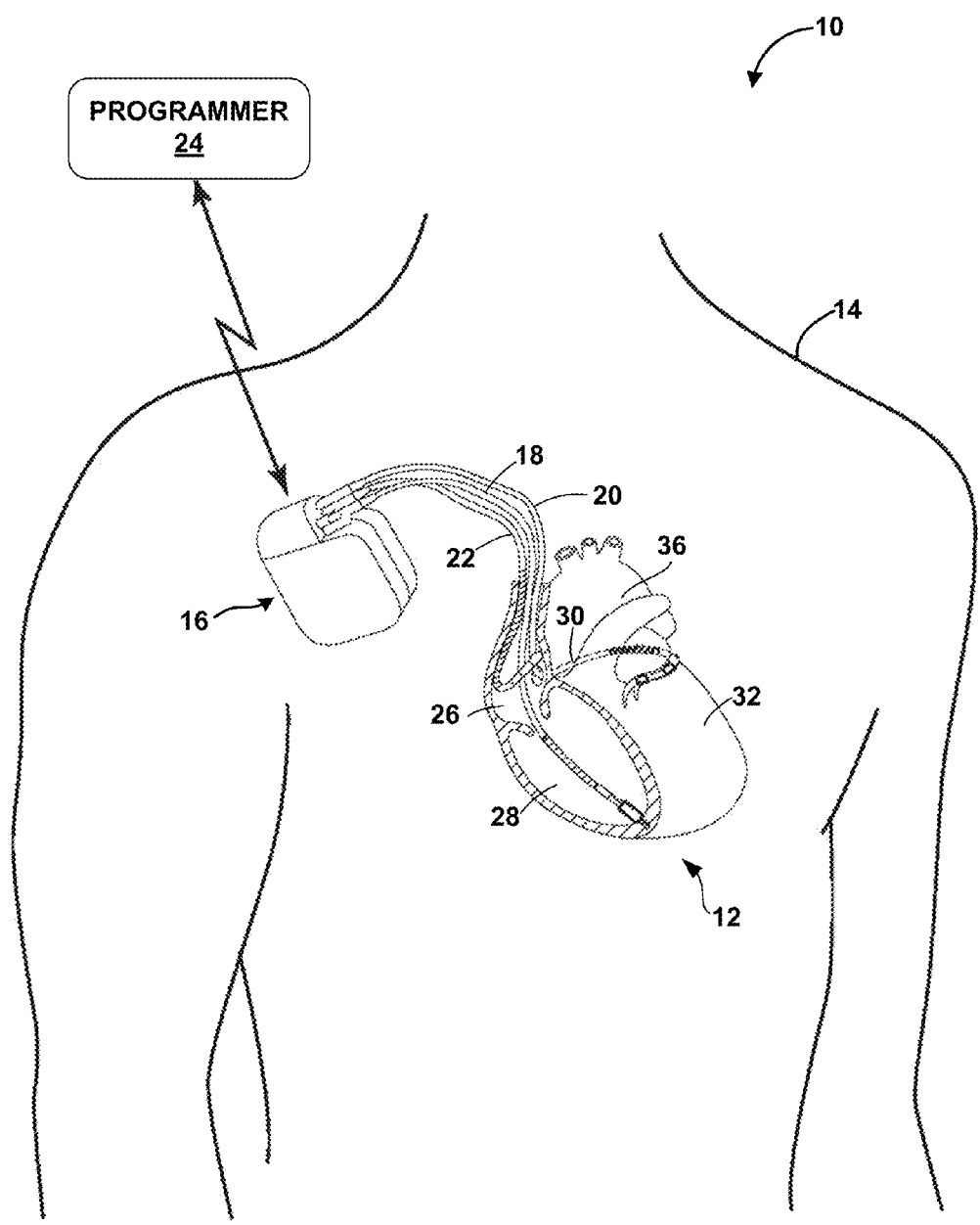
FIG. 1 is a conceptual drawing illustrating an example system that includes an implantable medical device (IMD) coupled to implantable medical leads.

This disclosure describes techniques and systems for quantifying autonomic tone of a patient with thoracic impedance measurements as an indication of autonomic nervous system (ANS) health. Since changes in autonomic tone can be used to indicate an improving or declining heart failure prognosis, thoracic impedance monitoring can provide valuable information to a clinician during diagnosis or treatment of many diseases and conditions. Further, thoracic impedance measurements may be obtained utilizing an implantable medical device already implanted to treat a cardiac condition of the patient.

Although heart rate and heart rate variability can be used as an indication of autonomic tone, heart rate measurements are only clinically relevant when the heart rate is determined by the activity of the SA node. When heart rate data is unavailable due to atrial tachyarrhythmia, or artificial pacing, a different measurement technique must be used to obtain an indication ANS health. This can be especially problematic in patients that have artificial pacing during most cardiac cycles. Measuring thoracic impedance allows for autonomic tone monitoring regardless of the patient's cardiac health and during periods of cardiac pacing.

Thoracic impedance may be measured in a variety of ways. For example, intrathoracic impedance may be measured between electrodes within the heart and the housing of the implantable medical device located within the thorax. Alternatively, impedance may be measured utilizing any two or more electrodes located on or within the patient's thoracic cavity, e.g., intrathoracic or transthoracic impedance measurements. In some examples, thoracic impedance may be measured using a subcutaneously implanted device, an externally mounted device, or any combination thereof. This impedance may be measured periodically over several days, weeks, or months for chronic ANS monitoring, in response to a change in patient posture or activity for acute monitoring, or in any other type of monitoring method appropriate for the patient's condition.

Greater variability or differences in thoracic impedance over time may indicate greater autonomic tone and better health of the ANS. Therefore, any changes in impedance or impedance variability can be used to quantify the relative autonomic tone of the patient and indicate to the clinician if heart failure is more or less probable. As examples, the difference in impedance can be measured between day and night impedances, over time in response to various posture changes or the same posture change, and the general impedance variability over time. An implantable medical device may independently analyze these impedance measurements and transmit an alert to the patient or clinician when impedance changes indicate a change in patient health. Alternatively, the implantable medical device may merely transmit stored impedance measurements to an external computing device for clinician analysis and review.

This techniques described in this disclosure may provide one or more advantages. For example, measuring thoracic impedance may allow a clinician to monitor autonomic tone in patients with atrial arrhythmia or artificial pacing. Since these patients may be at greater risk of heart failure, obtaining an early indication of declining health may be crucial to adjusting therapy and effectively treating the patient. Moreover, impedance measurements may be obtained with the use of a medical device needed by or already implanted in the patient. As described herein, intrathoracic impedance measurements may be taken between a intra-cardiac electrode and the electrically conductive housing of the implantable medical device, i.e., the pacemaker. In addition, the implantable medical device may issue an alert to the patient or clinician if the impedance measurements indicate that autonomic tone, and overall patient health, is declining.

FIG. 1 is a conceptual drawing illustrating an example system 10 that includes an implantable medical device (IMD) 16 for delivering therapy to heart 12 and capable of quantifying autonomic tone. Therapy system 10 includes IMD 16, which is coupled to leads 18, 20, and 22, and external programmer 24. IMD 16 may be, for example, an implantable pacemaker, cardioverter, and/or defibrillator that provides electrical signals to heart 12 via electrodes coupled to one or more of leads 18, 20, and 22. Patient 14 is ordinarily, but not necessarily, a human patient.

Although an implantable medical device and delivery of electrical stimulation to heart 12 are described herein as examples, the techniques for measuring thoracic impedance to quantify autonomic tone be applied using other medical devices and with or without other therapies. In general, the techniques described in this disclosure may be implemented by any medical device, e.g., implantable or external, that includes or is coupled to at least two electrodes to transmit and receive an electrical signal across a portion of the thorax of patient 14. As one alternative example, IMD 16 may be a neurostimulator that delivers electrical stimulation to and/or monitor conditions associated with the brain, spinal cord, or neural tissue of patient 16. As a second alternative example, IMD 16 may be a diagnostic device coupled to two subcutaneous electrodes at different positions in the thorax of patient 14 that monitors the intrathoracic impedance of patient 14, and does not deliver therapy to the patient.

In the example of FIG. 1, leads 18, 20, 22 extend into the heart 12 of patient 16 to sense electrical activity of heart 12, deliver electrical stimulation to heart 12, and/or measure intrathoracic impedance of patient 14. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, therapy system 10 may additionally or alternatively include one or more leads or lead segments (not shown in FIG. 1) that deploy one or more electrodes within the vena cava or other vein. These electrodes may allow alternative electrical sensing configurations that may provide improved or supplemental sensing in some patients. Furthermore, in some examples, therapy system 10 may additionally or alternatively include temporary or permanent epicardial or subcutaneous leads, instead of or in addition to transvenous, intracardiac leads 18, 20 and 22. Such leads may be used for one or more of cardiac sensing, pacing, cardioversion/defibrillation, and/or thoracic impedance measurement.

IMD 16 may sense electrical signals attendant to the depolarization and repolarization of heart 12 via electrodes (not shown in FIG. 1) coupled to at least one of the leads 18, 20, and 22. In some examples, IMD 16 provides pacing pulses to heart 12 based on the electrical signals sensed within heart 12. The configurations of electrodes used by IMD 16 for sensing and pacing may be unipolar or bipolar. IMD 16 may detect arrhythmia of heart 12, such as tachycardia or fibrillation of ventricles 28 and 32, and may also provide defibrillation therapy and/or cardioversion therapy via electrodes located on at least one of the leads 18, 20, and 22. In some examples, IMD 16 may be programmed to deliver a progression of therapies, e.g., pulses with increasing energy levels, until a fibrillation of heart 12 is stopped. IMD 16 may detect fibrillation employing one or more fibrillation detection techniques known in the art.

In some examples, programmer 24 comprises a handheld computing device, computer workstation, or networked computing device. Programmer 24 may include a user interface that receives input from a user. It should be noted that the user may also interact with programmer 24 remotely via a networked computing device.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16, such as stored thoracic impedance measurements and/or generated autonomic parameters. A user may also interact with programmer 24 to program IMD 16, e.g., select values for operational therapy parameters of the IMD and configure autonomic diagnostic functions.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20, and 22, or a power source of IMD 16. In some examples, this information may be presented to the user as an alert. For example, a lead related condition identified based on noise sensed subsequent to delivery of an electrical signal may trigger IMD 16 to transmit an alert to the user via programmer 24. In addition, a sensed decrease in thoracic impedance variability may trigger an alert to programmer 24 that there may be an increase in heart failure probability.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
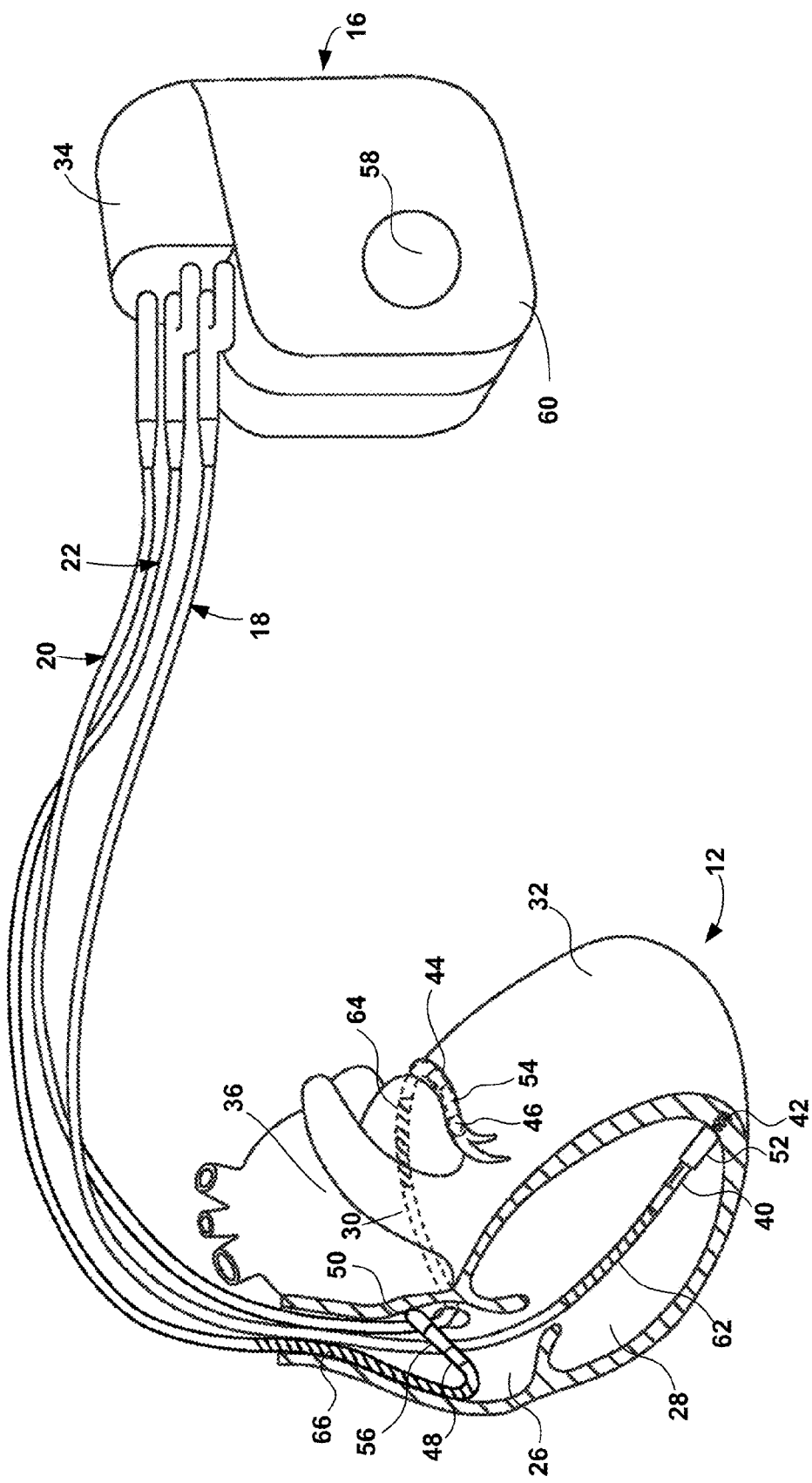
FIG. 2 is a conceptual drawing illustrating the example IMD and leads of FIG. 1 in conjunction with a heart.

FIG. 2 is a conceptual drawing illustrating IMD 16 and leads 18, 20, and 22 of system 10 in greater detail. Leads 18, 20, and 22 may be electrically coupled to a signal generator, e.g., stimulation generator, and a sensing module of IMD 16 via connector block 34. In some examples, proximal ends of leads 18, 20, and 22 may include electrical contacts that electrically couple to respective electrical contacts within connector block 34 of IMD 16. In addition, in some examples, leads 18, 20, and 22 may be mechanically coupled to connector block 34 with the aid of set screws, connection pins, snap connectors, or another suitable mechanical coupling mechanism.

Each of the leads 18, 20, and 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44, and 48 may take the form of ring electrodes, and electrodes 42, 46, and 50 may take the form of extendable helix tip electrodes mounted retractably within insulative electrode heads 52, 54, and 56, respectively. In other examples, one or more of electrodes 42, 46, and 50 may take the form of small circular electrodes at the tip of a tined lead or other fixation element. Leads 18, 20, and 22 also include elongated electrodes 62, 64, and 66, respectively, which may take the form of a coil. Each of the electrodes 40, 42, 44, 46, 48, 50, 62, 64, and 66 may be electrically coupled to a respective one of the coiled conductors within the lead body of its associated lead 18, 20, and 22, and thereby coupled to respective ones of the electrical contacts on the proximal end of leads 18, 20, and 22.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 4, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 62, 64, and 66. The electrical signals are conducted to IMD 16 from the electrodes via the respective leads 18, 20, and 22. IMD 16 may sense such electrical signals via any bipolar combination of electrodes 40, 42, 44, 46, 48, 50, 62, 64, and 66. Furthermore, any of the electrodes 40, 42, 44, 46, 48, 50, 62, 64, and 66 may be used for unipolar sensing in combination with housing electrode 58. The combination of electrodes used for sensing may be referred to as a sensing configuration.

In some examples, IMD 16 delivers pacing pulses via bipolar combinations of electrodes 40, 42, 44, 46, 48, and 50 to produce depolarization of cardiac tissue of heart 12. In other examples, IMD 16 delivers pacing pulses via any of electrodes 40, 42, 44, 46, 48, and 50 in combination with housing electrode 58 in a unipolar configuration. Furthermore, IMD 16 may deliver defibrillation pulses to heart 12 via any combination of elongated electrodes 62, 64, 66, and housing electrode 58. Electrodes 58, 62, 64, and 66 may also be used to deliver cardioversion pulses to heart 12. Electrodes 62, 64, and 66 may be fabricated from any suitable electrically conductive material, such as, but not limited to, platinum, platinum alloy or other materials known to be usable in implantable defibrillation electrodes. The combination of electrodes used for delivery of stimulation or sensing, their associated conductors and connectors, and any tissue or fluid between the electrodes, may define an electrical path.

The configuration of therapy system 10 illustrated in FIGS. 1 and 2 is merely one example. In other examples, a therapy system may include epicardial leads and/or patch electrodes instead of or in addition to the transvenous leads 18, 20, and 22 illustrated in FIG. 1. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

Figure 3:
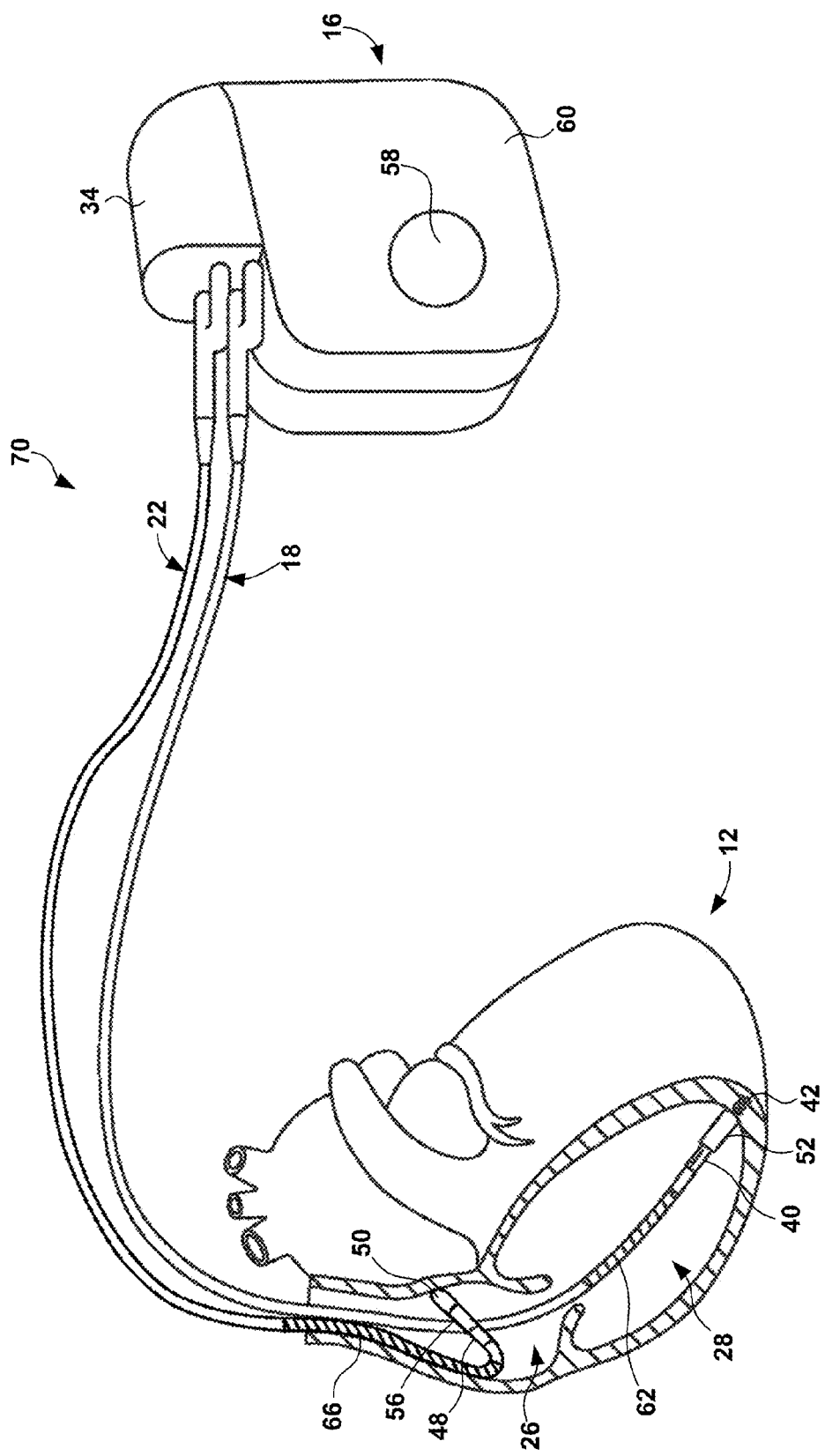
FIG. 3 is a conceptual drawing illustrating the example IMD of FIG. 1 coupled to a configuration of two implantable medical leads in conjunction with a heart.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36. As another example, other therapy systems may include a single lead that extends from IMD 16 into right atrium 26 or right ventricle 28, or two leads that extend into a respective one of the right ventricle 26 and right atrium 26. An example of this type of therapy system is shown in FIG. 3. Any electrodes located on these additional leads may be used in sensing and/or stimulation configurations.

In the example of FIG. 2, qualification of autonomic tone may be performed with the components already implanted to treat the heart condition of patient 14. IMD 16 may be configured to measure thoracic impedance, e.g., intrathoracic impedance, of patient 14. Thoracic impedance may comprise the electrical resistance (and, in some cases, reactance) across any portion of the thorax of patient 14 and is an indicator of fluid content within that portion of the thorax. Changes to thoracic impedance are related to acute fluid shifts that occur within the thorax that may be due to acute changes in vascular tone. Since the changes in vascular tone are presumably controlled by and indicative of the relative health of the ANS, measuring the thoracic impedance is an indirect quantification of ANS health. Further, an autonomic parameter may be generated as an index of autonomic tone and improving or declining ANS function from the measured thoracic impedance.

Although a longer electrical path through the thorax may be preferential the path distance between heart 12 and housing 60 may be sufficient to identify changes in thoracic impedance. In this manner, the electrical path used to measure thoracic impedance may be between any of electrodes 40, 42, 44, 46, 48, 50, 62, 64, or 66 and housing electrode 58. By utilizing an electrode already implanted within patient 14, autonomic tone may be monitored without any additional surgical procedures.

On example electrical path, or measurement vector, is a bipolar electrode arrangement between elongated electrode 62 in right ventricle 28 and housing electrode 58. When IMD 16 is implanted in the thorax close to the clavicle, the measurement vector may detect changes in intrathoracic fluid content indicative of autonomic tone. In other examples, the measurement vector may utilize electrodes 40 or 42 of right ventricle 28 instead of elongated electrode 62 to obtain the intrathoracic impedance measurement. Alternatively, any of the remaining cardiac electrodes 44, 46, 48, 50, 64, or 66 may be configured with housing electrode 58 to measure the thoracic impedance. Although IMD 16 is described as implanted in the superior chest region, IMD 16 may be implanted at any location within or proximate to the thorax of patient 14. For example, IMD 16 may be located in the abdomen of patient 14 to alter the electrical path between elongated electrode 62 and housing electrode 58.

In another example, a different thoracic electrode may be used in conjunction within housing electrode 58. One or more thoracic electrodes may be used instead of a cardiac electrode to measure thoracic impedance. For example, a thoracic electrode may be subcutaneously implanted in the thorax of patient 14 to be used in a bipolar arrangement with housing electrode 58. In addition, a second thoracic electrode may be implanted and used instead of housing electrode 58 to measure thoracic impedance with the other thoracic electrode. Thoracic electrodes may alternatively be implanted anywhere within the thorax of patient 14 or even adhered to the external surface of the skin proximate to the thorax. Thoracic electrodes may be electrically coupled to IMD 16 through a medical lead.

In other examples, thoracic electrodes may be connected to a small implanted module separate from, and in wireless communication with, the IMD. The impedance measuring device may measure thoracic impedance, generate autonomic parameters, and/or transmit the measured impedances or generated autonomic parameters to IMD 16. In any case, thoracic impedance may be measured through the operation of IMD 16 or with a device at least partially independent of IMD 16. In some examples, an external device may be coupled to external electrodes, measure thoracic impedance, e.g., transthoracic impedance, and otherwise implement the techniques described herein.

If the electrical path is altered due to the use of an alternative cardiac electrode 40, 42, 44, 46, 48, 50, 62, 64, or 66, the use of a different implanted thoracic electrode, or movement of the IMD 16 location, it may not be appropriate for new thoracic impedance measurements to be compared to previous measurements or generated autonomic parameters. This change in electrical path may be necessary if an electrode or corresponding medical lead fails to function properly or some other physiological difficulty prevents the use of the previous electrical path. Since the new electrical path may be of a different distance and travel through different organs, autonomic tone may only be monitored using the data from the new electrical path. However, in other embodiments, it may be possible to calibrate the impedance of the old electrical path to the new electrical path. For example, IMD 16 may be programmed to measure the thoracic impedance of the new electrical path at two different patient 14 postures and compare these measurements to recently stored measurements from the old electrical path. IMD 16 may then generate a scaling factor or other formula that can be used to calibrate the old thoracic impedance measurements to new measurements from the new electrical path. In this manner, calibration may allow the clinician to continually use prior autonomic parameters to diagnose and treat patient 14.

Additionally, as previously mentioned, IMD 16 need not deliver therapy to heart 12. In general, this disclosure may be applicable to any medical device, e.g., implantable or external, that includes electrodes to sense physiological signals, deliver electrical stimulation to patient 14, and/or measure intrathoracic impedance.

FIG. 3 is a conceptual diagram illustrating another example of therapy system 70, which is similar to therapy system 10 of FIGS. 1 and 2, but includes two leads 18 and 22, rather than three leads. Leads 18 and 22 are implanted within right ventricle 28 and right atrium 26, respectively. Therapy system 70 shown in FIG. 3 may be useful for providing defibrillation and pacing pulses to heart 12. Measurement of thoracic impedance and the generation of autonomic parameters may be performed in two lead systems, such as system 70, in the same manner as that described herein with respect to three lead systems. In addition, other thoracic electrodes may also be used to measure the thoracic impedance as described in FIG. 2.

Figure 4:
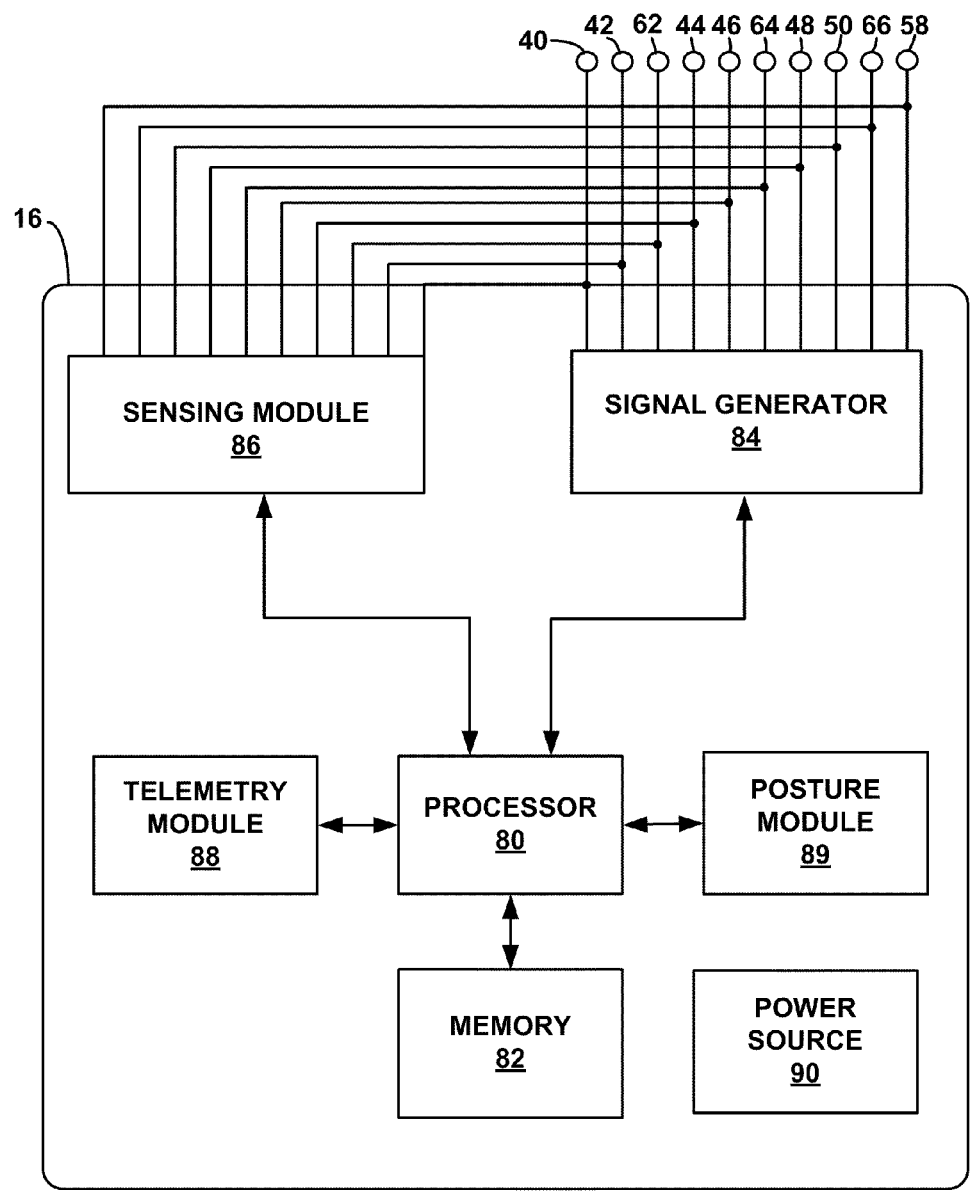
FIG. 4 is a functional block diagram illustrating an example configuration of the IMD of FIG. 1.

FIG. 4 is a functional block diagram illustrating an example configuration of IMD 16. In the illustrated example, IMD 16 includes a processor 80, memory 82, signal generator 84, sensing module 86, telemetry module 88, posture module 89, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver stimulation therapy to heart 12 according to a selected one or more of therapy programs, which may be stored in memory 82. For example, processor 80 may control stimulation generator 84 to deliver electrical pulses with the amplitudes, pulse widths, frequency, or electrode polarities specified by the selected one or more therapy programs.

Signal generator 84 is electrically coupled to electrodes 40, 42, 44, 46, 48, 50, 58, 62, 64, and 66, e.g., via conductors of the respective lead 18, 20, and 22, or, in the case of housing electrode 58, via an electrical conductor disposed within housing 60 of IMD 16. In the illustrated example, signal generator 84 is configured to generate and deliver electrical stimulation therapy to heart 12. For example, signal generator 84 may deliver defibrillation shocks to heart 12 via at least two electrodes 58, 62, 64, and 66. Signal generator 84 may deliver pacing pulses via ring electrodes 40, 44, and 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Electrical sensing module 86 monitors signals from at least one of electrodes 40, 42, 44, 46, 48, 50, 58, 62, 64 or 66 in order to monitor electrical activity of heart 12. Sensing module 86 may also include a switch module to select which of the available electrodes are used to sense the heart activity, depending upon which electrode combination is used in the current sensing configuration. In some examples, processor 80 may select the electrodes that function as sense electrodes, i.e., select the sensing configuration, via the switch module within sensing module 86. Processor 80 may control the functionality of sensing module 86 by providing signals via a data/address bus.

Sensing module 86 may include one or more detection channels, each of which may comprise an amplifier. The detection channels may be used to sense the cardiac signals. Some detection channels may detect events, such as R- or P-waves, and provide indications of the occurrences of such events to processor 80. One or more other detection channels may provide the signals to an analog-to-digital converter, for processing or analysis by processor 80. In response to the signals from processor 80, the switch module within sensing module 86 may couple selected electrodes to selected detection channels.

For example, sensing module 86 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 80 then uses that detection in measuring frequencies of the sensed events. Different narrow band channels of sensing module 86 may have distinct functions. For example, some various narrow band channels may be used to sense either atrial or ventricular events.

In one example, at least one narrow band channel may include an R-wave amplifier that receives signals from the sensing configuration of electrodes 40 and 42, which are used for sensing and/or pacing in right ventricle 28 of heart 12. Another narrow band channel may include another R-wave amplifier that receives signals from the sensing configuration of electrodes 44 and 46, which are used for sensing and/or pacing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, a narrow band channel may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

In some examples, sensing module 86 includes a wide band channel which may comprise an amplifier with a relatively wider pass band than the R-wave or P-wave amplifiers. Signals from the selected sensing electrodes that are selected for coupling to this wide-band amplifier may be converted to multi-bit digital signals by an analog-to-digital converter (ADC) provided by, for example, sensing module 86 or processor 80. In some examples, processor 80 may store signals the digitized versions of signals from the wide band channel in memory 82 as electrograms (EGMs).

In some examples, processor 80 may employ digital signal analysis techniques to characterize the digitized signals from the wide band channel to, for example detect and classify the patient's heart rhythm. Processor 80 may detect and classify the patient's heart rhythm by employing any of the numerous signal processing methodologies known in the art.

Processor 80 may maintain one or more programmable interval counters. If IMD 16 is configured to generate and deliver pacing pulses to heart 12, processor 80 may maintain programmable counters which control the basic time intervals associated with various modes of pacing, including cardiac resynchronization therapy (CRT) and anti-tachycardia pacing (ATP). In examples in which IMD 16 is configured to deliver pacing therapy, intervals defined by processor 80 may include atrial and ventricular pacing escape intervals, refractory periods during which sensed P-waves and R-waves are ineffective to restart timing of the escape intervals, and the pulse widths of the pacing pulses. As another example, processor 80 may define a blanking period, and provide signals to sensing module 86 to blank one or more channels, e.g., amplifiers, for a period during and after delivery of electrical stimulation to heart 12. The durations of these intervals may be determined by processor 80 in response to stored data in memory 82. Processor 80 may also determine the amplitude of the cardiac pacing pulses.

Processor 80 may reset interval counters upon sensing of R-waves and P-waves with detection channels of sensing module 86. For pacing, signal generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. Processor 80 may also reset the interval counters upon the generation of pacing pulses by signal generator 84, and thereby control the basic timing of cardiac pacing functions, including CRT and ATP.

The value of the count present in the interval counters when reset by sensed R-waves and P-waves may be used by processor 80 to measure the durations of R-R intervals, P-P intervals, PR intervals and R-P intervals, which are measurements that may be stored in memory 82. Processor 80 may use the count in the interval counters to detect a tachyarrhythmia event, such as ventricular fibrillation or ventricular tachycardia. In some examples, a portion of memory 82 may be configured as a plurality of recirculating buffers, capable of holding series of measured intervals, which may be analyzed by processor 80 to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies may also be employed by processor 80 in other examples.

In some examples, processor 80 may determine that tachyarrhythmia has occurred by identification of shortened R-R (or P-P) interval lengths. Generally, processor 80 detects tachycardia when the interval length falls below 220 milliseconds (ms) and fibrillation when the interval length falls below 180 ms. These interval lengths are merely examples, and a user may define the interval lengths as desired, which may then be stored within memory 82. This interval length may need to be detected for a certain number of consecutive cycles, for a certain percentage of cycles within a running window, or a running average for a certain number of cardiac cycles, as examples.

Processor 80 may also control signal generator 84 and sensing module 86 to measure the thoracic impedance between two or more electrodes. For example, processor 80 may cause signal generator 84 to generate an electrical signal of known current or voltage, and apply the signal to the electrodes. Processor 80 may control sensing module 86 to measure a resulting voltage or current, from which processor 80 may determine an impedance that includes the impedance between the electrodes, i.e., the thoracic impedance. As described herein, an example bipolar electrode combination for measuring the thoracic impedance would be elongated electrode 62 as the first electrode and housing electrode 58 as the second electrode. In other examples, processor 80 may take any alternative approach to impedance measurement known in the art. In some examples, processor 80 need not calculate impedance, and instead may, for example, monitor variations in measured current or voltage.

The signal generated by signal generator 84 for impedance measurements may comprise one or more pulses or continuous time signals, e.g., sine waves. The signal may be sub-threshold, e.g., below a threshold amplitude and/or pulse width necessary to capture tissue, e.g., the heart. Additionally or alternatively, the signal may be delivered during a period in which the heart is refractory.

IMD 16 also supports the measurement of thoracic impedance during delivery of therapy to patient 14, such as atrial pacing therapy. Processor 80 may monitor the pacing stimulation generated and delivered by signal generator 84 to determine the appropriate timing of an thoracic impedance measurement. Preferably, the measurement of thoracic impedance will not interfere with any provided therapy. In some examples, processor 80 may obtain thoracic impedance values at multiple times during a cardiac cycle in order to get an average impedance value. Alternatively, processor 80 may time any thoracic impedance measurement to always take place during the same period of the cardiac cycle to minimize the introduction of cardiac function variability into the measured thoracic impedance. In some examples, processor 80 may use pacing pulses as the signal for impedance measurements, e.g., by controlling sensing module 86 to measure a voltage or current during delivery of the pacing pulse having a known current or voltage.

The thoracic impedance measurements described herein may be taken using any number of measurement vectors.

These vectors may between electrodes within the heart, outside the heart, within the vasculature, or any combination thereof. These vectors may also be between electrodes implanted within patient 14, placed on the external skin of patient 14, or a combination in implanted and external electrodes. Any of these types of sensing vectors may be used to generate the thoracic impedance measurements. Although the difference of thoracic impedance value is generally described herein, other attributes of impedance such as the phase of the impedance signal may also be used to analyze changes in ANS health.

Processor 80 may then store the measured thoracic impedance in memory 82 along with previously measured thoracic impedances. Memory 82 may store the measured thoracic impedances along with other operational instructions or memory 82 may include a separate memory for storing the thoracic impedances. If memory 82 has reached capacity, memory 82 may replace the oldest stored thoracic impedance with the new thoracic impedance to prevent the discarding of the newest measurement.

In addition, processor 80 may generate an autonomic parameter based upon the measured thoracic impedance and at least one previously measured thoracic impedance value. This autonomic parameter may be the change in impedance amplitude, the variance in impedance values, the standard deviation of impedance values, the standard error of impedance values, the trend of impedance values (e.g., the magnitude of the slope), the rolling average of impedance values, the maximum change in impedance over a certain period of time, the difference between day impedance and night impedance values, or any other indication of impedance changes. Any and all of these autonomic parameters may also be stored in memory 82 when generated by processor 80.

In chronic monitoring mode, processor 80 may periodically obtain thoracic impedance measurements to monitor any changes in health of the ANS. The periodic determination may be any regular interval preferred by the clinician. For example, processor 80 may schedule thoracic impedance measurements every minute, hour, day, or week depending on the condition of patient 14. Alternatively, processor 80 may even obtain the thoracic impedance value multiple times within the same second. Frequent impedance values may be averaged over a period of time to obtain hourly or daily averages, for example. Processor 80 may alter the measurement of thoracic impedance if therapy changes for any reason. Processor 80 may compare autonomic parameters to determine of the ANS health is improving, worsening, or staying generally steady.

In an acute monitoring mode, processor 80 may obtain posture information from posture module 89 to determine when to obtain or store intrathoracic impedance values. Since the ANS modulates vascular tone, a healthy ANS adjusts vascular tone throughout patient 14 in order to maintain proper blood pressure at all locations within patient 14. Changes in posture or activity may indicate that there already has been or there will be a change to thoracic impedance given sufficient autonomic tone. For example, an orthogonally positioned accelerometer may be configured to detect a sudden change in patient posture and trigger a thoracic impedance measurement. Therefore, processor 80 may begin measuring and storing thoracic impedance and/or permanently store any impedance measurements obtained and temporarily stored just prior to a change in posture.

In other examples, processor 80 may additionally or alternatively obtain other physiological information from patient 14 to determine when to obtain or store thoracic impedance values. For example, processor 80 may identify changes in heart rate, temperature, or breathing rates, the occurrence of a tachyarrhythmia, or premature ventricular complexes, or any other physiological attribute or event, and obtain and/or store a thoracic impedance measurement in response to the identified attribute or event in the same manner described herein with respect to posture or posture changes. In some examples, IMD 16 may include other sensors to detect such physiological events or attributes, such as pressure sensors, temperature sensors, or oxygen saturation sensors. Any detected changes in thoracic impedance over time, or temporal changes, may be used by processor 80 to determine ANS health or other baroreflex sensitivity.

Posture module 89 is configured to detect the position of patient 14 and output a representative signal of the physiological parameter to processor 80. Posture module 89 may be any sensor capable of determining the position or activity level. For example, posture module 89 may be a single-axis or multi-axis accelerometer, multiple accelerometers, a bonded piezoelectric crystal, a mercury switch, or a gyroscope. A change in posture may include patient 14 moving from one static position to a different static position or a change in the activity state of patient 14. For example, the posture change type may include standing up, sitting up, sitting down, reclining back, laying down, starting to exercise, and stopping exercise. Example activities may include sitting, laying down, walking, running, riding a bike, swimming, driving, or any other activity that the clinician may desire to correlate to autonomic tone.

Posture module 89 may allow processor 80 to generate useful information regarding changes in autonomic tone in response to posture changes. For example, processor 80 may correlate impedance changes to specific posture change types and monitor thoracic impedance variations within that specific posture change type. In this manner, processor 80 may be able to identify reduced or improved autonomic tone where it may not be discernable when monitoring chronic autonomic tone.

In some examples, processor 80 may provide an alert to a user, e.g., of programmer 24 or other computing device, regarding the thoracic impedance measurement or generated autonomic parameter when the condition of patient 14 has changed. Processor 80 may compare autonomic parameters to predetermined thresholds and transmit an alert when ANS health has declined below the threshold. In receiving the alert, the clinician can determine if there needs to be a change in stimulation therapy, drug therapy, or any other therapy to treat the decline in ANS health.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., electrocardiogram signals) produced by atrial and ventricular sense amp circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac events that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

In addition, processor 80 may transmit information regarding the measured thoracic impedances or generated autonomic parameters to programmer 24 via telemetry module 88. For example, processor 80 may provide an alert that the autonomic parameter, e.g., impedance variability, has fallen below a predetermined threshold, suggest that autonomic tone be monitored in a different method, or suggest that electrical stimulation or drug therapy be adjusted in order to compensate for the change in autonomic tone to programmer 24 via telemetry module 88. Processor 80 may also receive information regarding patient 14 autonomic tone or responses to such conditions from programmer 24 via telemetry module 88. In addition, processor 80 may receive intrathoracic impedance data or measurements from other implantable medical devices via telemetry module 88.

In some examples, IMD 16 may signal programmer 24 to further communicate with and pass the alert through a network such as the Medtronic CareLink® Network developed by Medtronic, Inc., of Minneapolis, Minn., or some other network linking patient 14 to a clinician.

Figure 5:
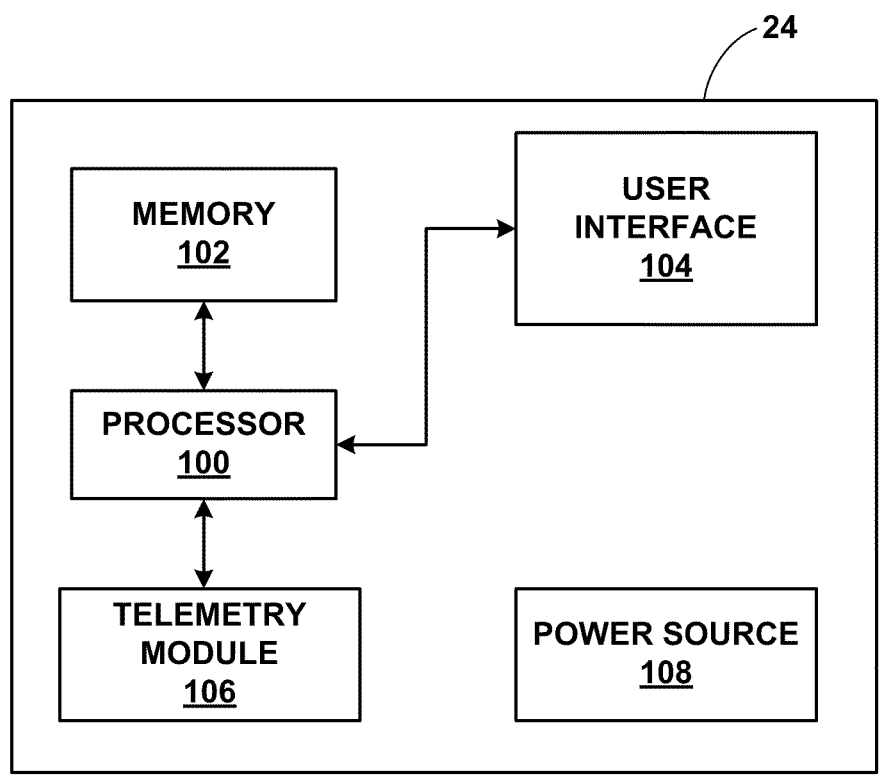
FIG. 5 is a functional block diagram illustrating an example configuration of an external programmer that facilitates user communication with the IMD.

FIG. 5 is functional block diagram illustrating an example configuration of programmer 24. As shown in FIG. 5, programmer 24 may include a processor 100, memory 102, user interface 104, telemetry module 106, and power source 108. Programmer 24 may be a dedicated hardware device with dedicated software for programming of IMD 16. Alternatively, programmer 24 may be an off-the-shelf computing device running an application that enables programmer 24 to program IMD 16. In some other examples, programmer 24 is a computing device capable of receiving thoracic impedances and/or autonomic parameters from IMD 16 and/or an additional medical device that contributes to impedance measurement.

A user may use programmer 24 to select values of operational parameters. The clinician may interact with programmer 24 via user interface 104, which may include display to present graphical user interface to a user, and a keypad or another mechanism for receiving input from a user.

The user may also use programmer 24 to adjust or control the measurement of thoracic impedances and generation of autonomic parameters to quantify the autonomic tone of patient 14. Programmer 24 may also set any instructions that govern the issuance of autonomic tone alerts. For example, the user may use programmer 24 to determine the frequency of periodic thoracic impedance measurement during chronic monitoring. In another example, the user may use programmer 24 to select the one or more autonomic parameters used to monitor autonomic tone. If programmer 24 is a patient programmer, the patient may have limited control over the adjustment of autonomic tone monitoring. However, the patient would still be able to receive alerts on their condition.

Upon receiving an autonomic tone alert from IMD 16, programmer 24 may provide suggestions to the user to remedy the problem. If programmer 24 is used by the clinician, programmer 24 may present multiple suggested changes in pacing therapy, drug therapy, or patient lifestyle to limit the effect of declining ANS health. If programmer 24 is used by patient 14, programmer 24 may suggest a specific posture to remain in, a posture to avoid, and/or to contact their clinician.

User interface 104 may present thoracic impedances and/or autonomic parameters to the user. This information may be presented numerically, graphically, or both. In addition, the user may select how the information is presented in order to fully understand any changes in ANS health as indicated by the changes in autonomic tone. In this manner, the information presented on user interface 104 may be interactive and adjustable as the user desires. Examples of graphical information presented on programmer 24 may include the illustrations of example FIGS. 7-9.

Processor 100 can take the form one or more microprocessors, DSPs, ASICs, FPGAs, programmable logic circuitry, or the like, and the functions attributed to processor 100 herein may be embodied as hardware, firmware, software or any combination thereof. Memory 102 may store instructions that cause processor 100 to provide the functionality ascribed to programmer 24 herein, and information used by processor 100 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient.

Programmer 24 may communicate wirelessly with IMD 16, such as using RF communication or proximal inductive interaction. This wireless communication is possible through the use of telemetry module 106, which may be coupled to an internal antenna or an external antenna. An external antenna that is coupled to programmer 24 may correspond to the programming head that may be placed over heart 12, as described above with reference to FIG. 1. Telemetry module 106 may be similar to telemetry module 88 of IMD 16 (FIG. 4).

Telemetry module 106 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In some examples, processor 100 of programmer 24 and/or one or more processors of one or more networked computers may perform all or a portion of the techniques described herein with respect to processor 80 and IMD 16. For example, processor 100 or another processor may receive thoracic impedances or other sensed signals from IMD 16 for evaluation of autonomic tone.

Figure 6:
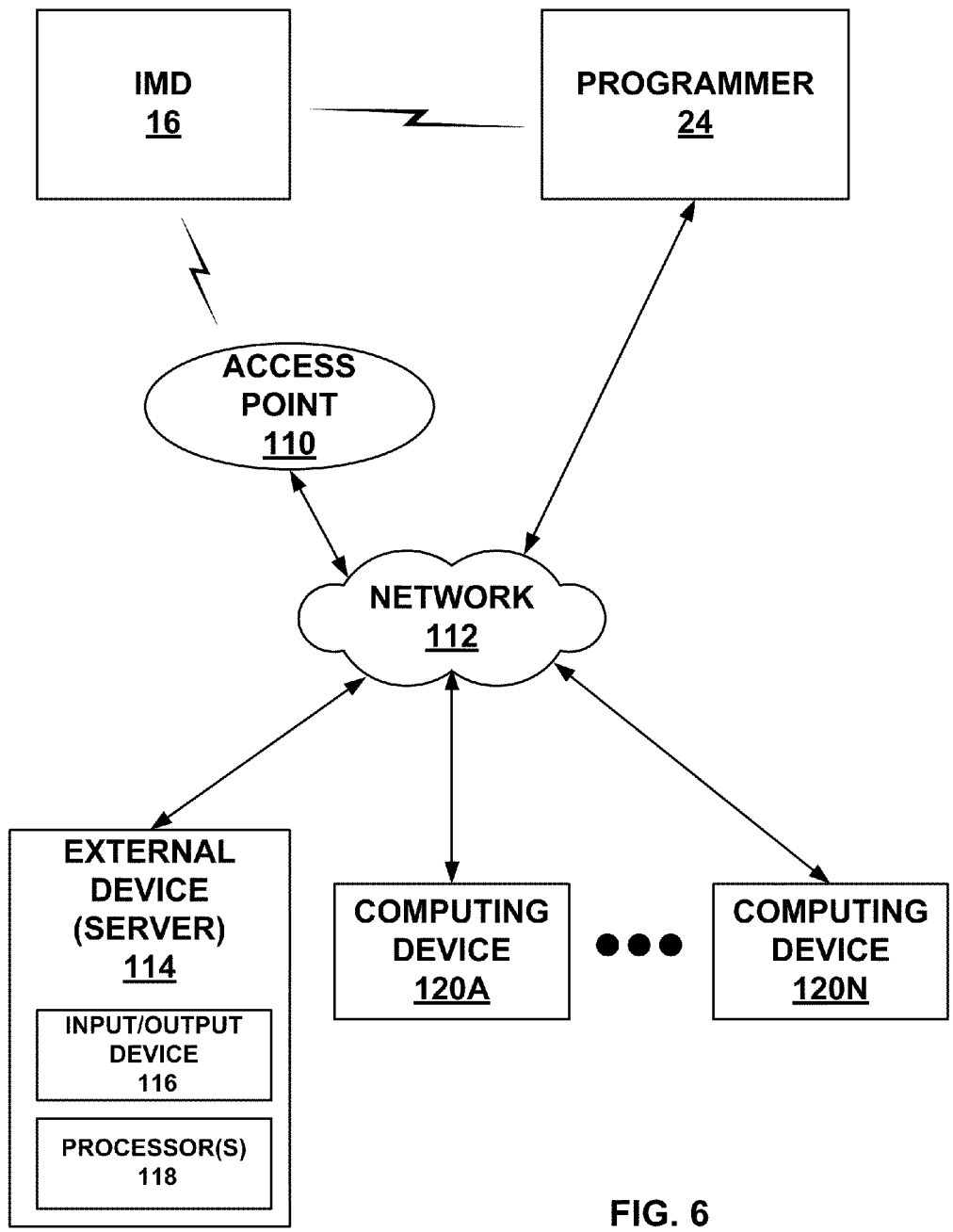
FIG. 6 is a block diagram illustrating an example system that includes an external device, such as a server, and one or more computing devices that are coupled to the IMD and programmer shown in FIG. 1 via a network.

FIG. 6 is a block diagram illustrating an example system that includes an external device, such as a server 114, and one or more computing devices 120A-120N, that are coupled to the IMD 16 and programmer 24 shown in FIG. 1 via a network 112. In this example, IMD 16 may use its telemetry module 88 to communicate with programmer 24 via a first wireless connection, and to communication with an access point 110 via a second wireless connection. In the example of FIG. 6, access point 110, programmer 24, server 114, and computing devices 120A-120N are interconnected, and able to communicate with each other, through network 112. In some cases, one or more of access point 110, programmer 24, server 114, and computing devices 120A-120N may be coupled to network 112 through one or more wireless connections. IMD 16, programmer 24, server 114, and computing devices 120A-120N may each comprise one or more processors, such as one or more microprocessors, DSPs, ASICs, FPGAs, programmable logic circuitry, or the like, that may perform various functions and operations, such as those described herein.

Access point 110 may comprise a device that connects to network 112 via any of a variety of connections, such as telephone dial-up, digital subscriber line (DSL), or cable modem connections. In other embodiments, access point 110 may be coupled to network 112 through different forms of connections, including wired or wireless connections. In some embodiments, access point 200 may be co-located with patient 14 and may comprise one or more programming units and/or computing devices (e.g., one or more monitoring units) that may perform various functions and operations described herein. For example, access point 110 may include a home-monitoring unit that is co-located with patient 14 and that may monitor the activity of IMD 16. In some embodiments, server 114 or computing devices 120 may control or perform any of the various functions or operations described herein, e.g., control performance of thoracic impedance measurements by IMD 16 or analyze impedance measurements made by IMD 16.

In some cases, server 114 may be configured to provide a secure storage site for archival of thoracic impedances and autonomic parameters that have been collected from IMD 16 and/or programmer 24. Network 112 may comprise a local area network, wide area network, or global network, such as the Internet. In some cases, programmer 24 or server 114 may assemble autonomic parameters or autonomic tone information in web pages or other documents for viewing by and trained professionals, such as clinicians, via viewing terminals associated with computing devices 120. The system of FIG. 6 may be implemented, in some aspects, with general network technology and functionality similar to that provided by the Medtronic CareLink® Network developed by Medtronic, Inc., of Minneapolis, Minn.

Figure 7A:
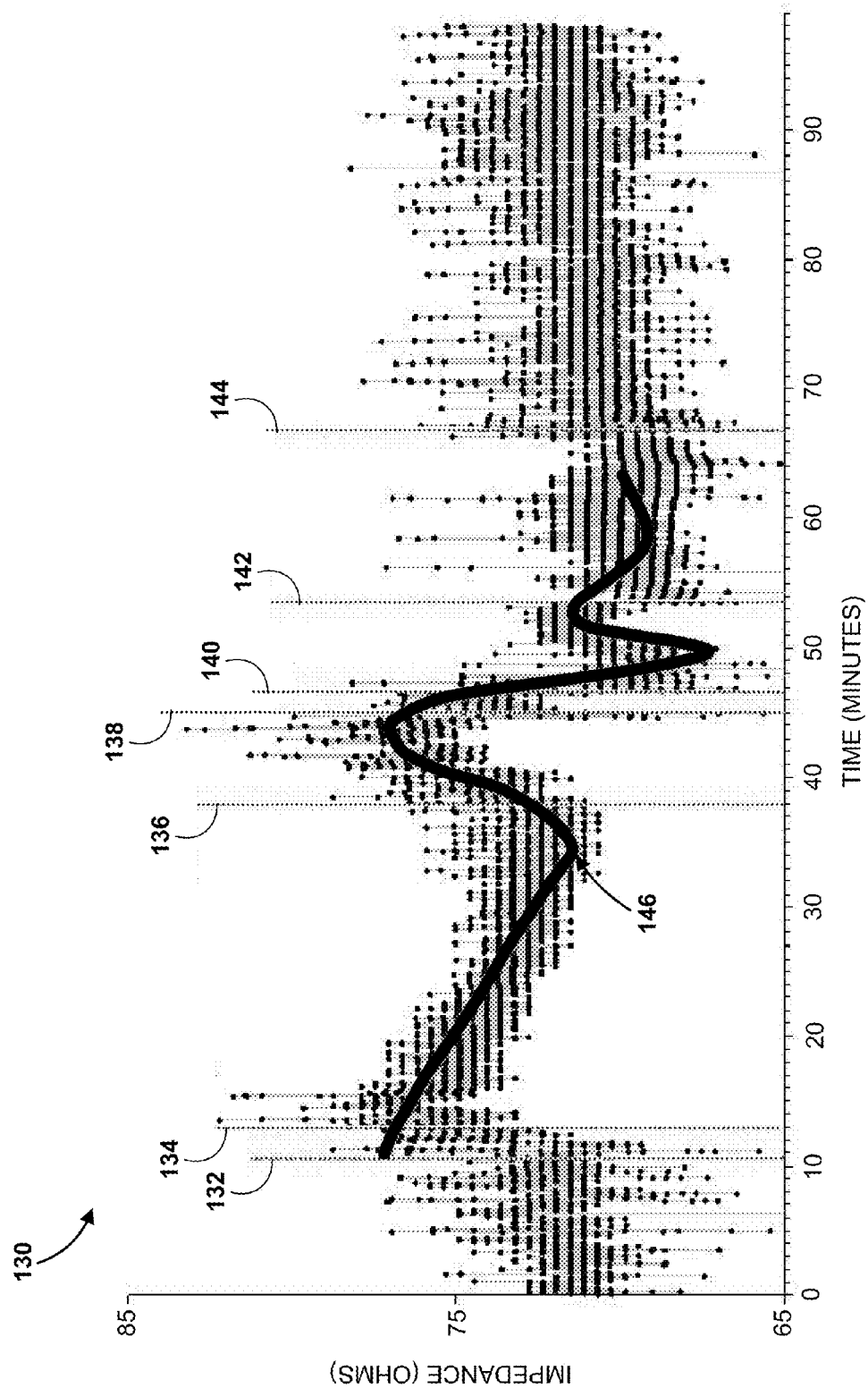
FIGS. 7A and 7B illustrate example thoracic impedance measurements resulting from posture changes in a patient with a relatively healthy ANS.
Figure 7B:
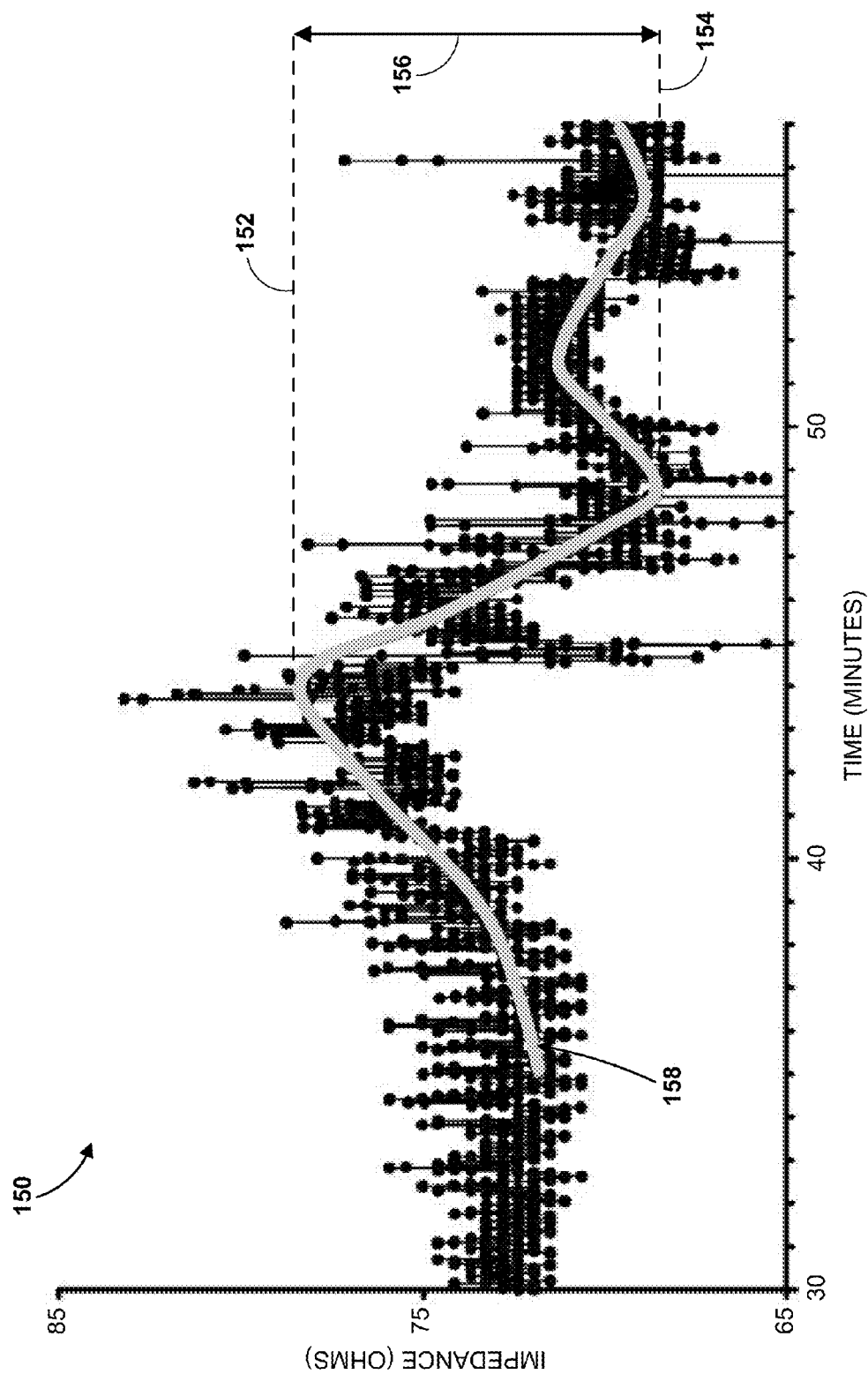

FIGS. 7A and 7B illustrate example thoracic impedance measurements from Experiment 1 resulting from posture changes in patient A with a relatively healthy ANS. In the examples of FIGS. 7A and 7B, the amplitude of changes in intrathoracic impedance values may be the autonomic parameter used as the index of autonomic tone.

As shown in FIG. 7A, graph 130 provides measured thoracic impedance values over time for the example patient A. Impedance values are provided in Ohms, and generally are between 65 and 85 Ohms. Impedance was measured between the right ventricular defibrillation coil and IMD 16 housing, i.e., elongated electrode 62 and housing electrode 58, and patient A underwent a variety of posture and activity changes during a ninety minute period. General variation 146 is a line that indicates the average impedance between the continual variations in beat to beat impedance measurements. The variation in impedance between consecutive measurements is at least partially due to lung volume changes during breathing. Variation due to breathing may be removed by analog or digital smoothing or filtering, e.g., provided by processor 80 or sensing module 86, in some examples.

At time interval 132, patient A begins lying in the supine position for 30 minutes and subsequently begins breathing at time interval 134. During this period, average line 146 indicates a gradual decline in thoracic impedance due to increased fluid content in the thorax of patient A. However, impedance begins to increase just before patient A wakes up from a 5 minute sleep at time interval 136. General variation 146 continues to increase until patient A changes posture from the supine position to an upright position by standing up at time interval 138. Patient A then sits on a stationary bike at time interval 140 and begins exercising by pedaling the bike at time interval 142. At time interval 144, patient A stops pedaling.

General variation 146 indicates that the thoracic impedance of patient A is changing due to changes in posture, including undertaking different activities. Although the intrathoracic impedance of patient A, as indicated by general variation 146, decreases somewhat when patient A is in the supine position between time intervals 132 and 136 and when patient A is exercising between time intervals 142 and 144, the largest variations in impedance occur during the relatively brief periods in which patient A changes posture, e.g., standing up from a supine position at time interval 138 and sitting on a bike at interval 140. These changes in thoracic impedance may indicate that the ANS of patient A is capable of regulating thoracic fluid levels in response to, or in anticipation of, changes to posture.

As shown in FIG. 7B, graph 150 provides a portion of graph 130 from FIG. 7A. General variation 158 indicates the acute change in average thoracic impedance between time intervals 136 and 144 of FIG. 7A. Amplitude 156 is the measured change in intrathoracic impedances between high value 152 and low value 154. Amplitude 156 may be used as the autonomic parameter that quantifies the autonomic tone of patient A. Here, amplitude 156 is approximately 10 Ohms.

Specifically amplitude 156 may be correlated to the posture change type responsible for the change in thoracic impedance. As shown in FIG. 7A, the large change in impedance was caused by patient A changing from standing to sitting on the stationary bike. For example, posture module 89 may detect this change in posture and processor 80 of IMD 16 may generate the autonomic parameter of amplitude 156 after measuring the changes in thoracic impedance. In an acute monitoring mode, IMD 16 may then compare amplitude 156 to prior amplitudes stored for the same change in posture, or posture change type. A decrease in amplitude may indicate a degradation in autonomic tone and general ANS health, and an increase in heart failure probability. Conversely, an increase in amplitude may indicate an improvement in autonomic tone and ANS health.

In some examples, IMD 16 may generate further autonomic parameters off of the thoracic impedance values obtained in graphs 130 and 150. IMD 16 may simultaneously monitor several types of autonomic parameters to best monitor any changes in the health of the patient.

Figure 8:
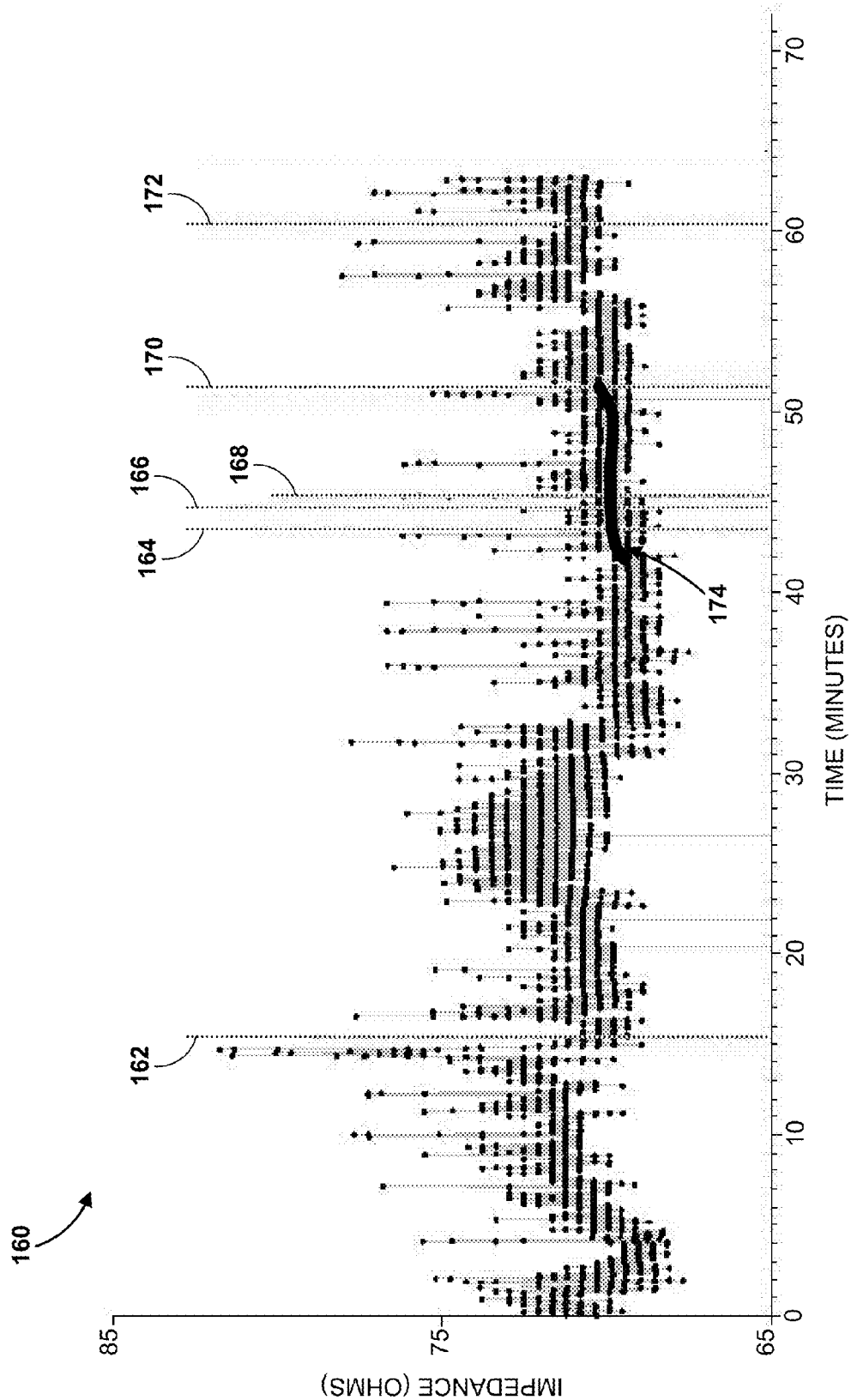
FIG. 8 illustrates example thoracic impedance measurements resulting from posture changes in a patient with decreased autonomic tone.

FIG. 8 illustrates example thoracic impedance measurements resulting from posture changes in a patient with decreased autonomic tone. As shown in FIG. 8, graph 160 provides measured thoracic impedance values over time for the example patient B (similar to FIG. 7A). Impedance values are provided in Ohms, and generally are between 65 and 85 Ohms. Impedance was measured between the right ventricular defibrillation coil and IMD 16 housing, i.e., elongated electrode 62 and housing electrode 58, and patient B underwent a variety of posture and activity changes during a seventy minute period. General variation 174 is a line that indicates the average impedance between the continual variations in beat to beat impedance measurements. The variation in impedance between consecutive measurements is at least partially due to lung volume changes during breathing.

At time interval 162, patient B is resting in a supine posture. At time interval 164, patient B moves to a seated posture until patient B stands up at time interval 166. Patient B then gets on a stationary bike at time interval 168 and starts exercising by pedaling the bike at time interval 170. At time interval 172, patient B stops exercising.

As indicated by general variation 174, the thoracic impedance of patient B does not change much in response to posture changes. In fact, the amplitude of the change in general variability 174 from posture changes, or the autonomic parameter, is essentially zero. In comparison to patient A from FIGS. 7A and 7B, patient B may have worse autonomic tone due to diminished ANS health. Patient B may be at a higher risk for heart failure. During acute monitoring, further autonomic parameters could be generated from thoracic impedance measurements to determine if the autonomic tone of patient B could increase. In some cases where a patient exhibits minimal changes in impedance amplitude as a result of a few posture change types, e.g., standing up and sitting down in FIG. 8, IMD 16 may look for other posture change types that have a change in impedance amplitude so that further decreases in autonomic tone could be monitored in a patient like patient B of FIG. 8.

Figure 9:
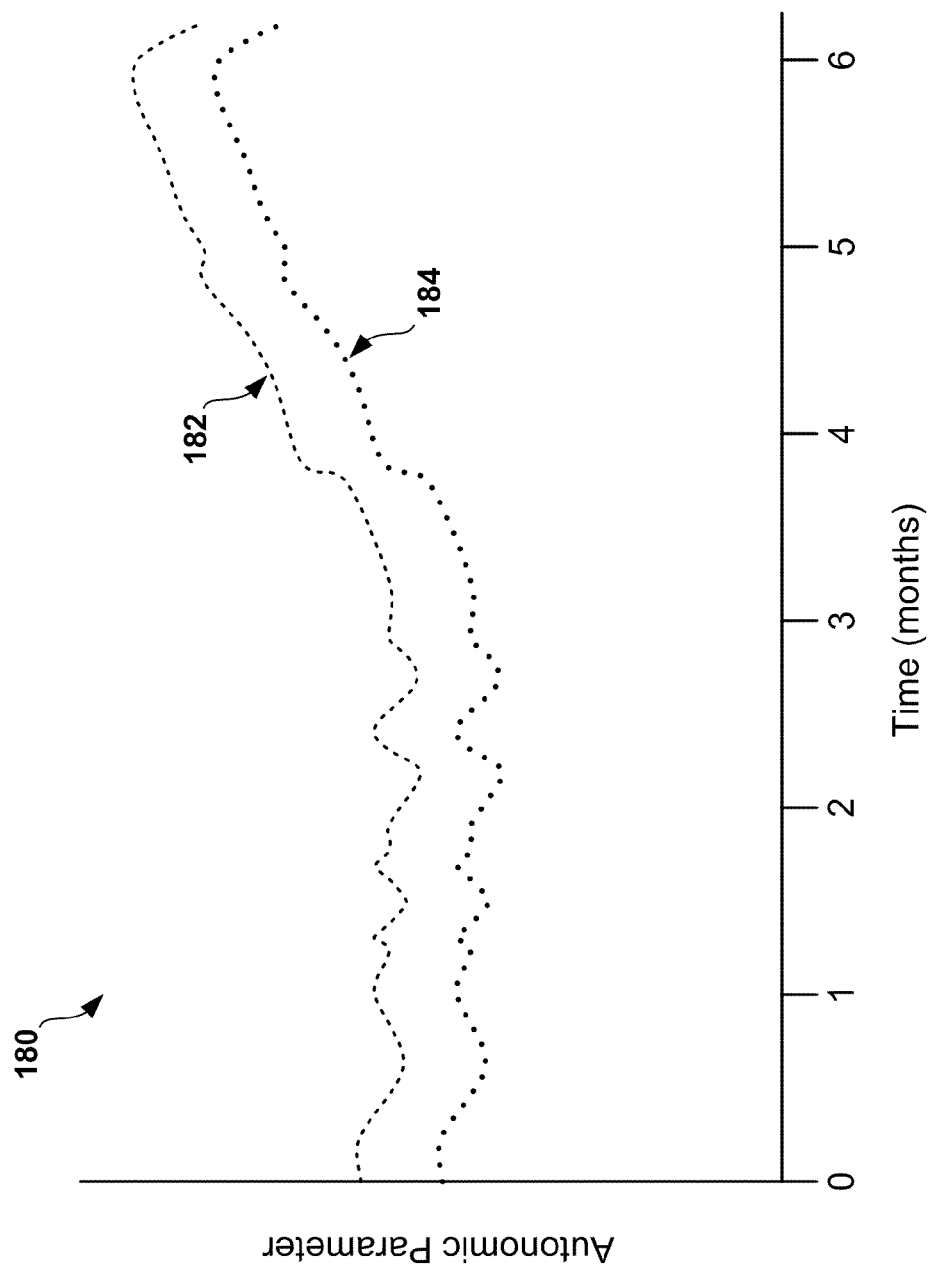
FIG. 9 illustrates an example graph of impedance variability separated by daytime and nighttime measurements.

FIG. 9 illustrates an example graph 180 of impedance variability separated by time of day. As shown in FIG. 9, thoracic impedance has been chronically monitored for patient 14. Thoracic impedance has been periodically obtained one or more time per day over a six month period, and IMD 16 has generated an impedance variability autonomic parameter for the daytime hours (when patient 14 is awake) and the nighttime hours (when patient 14 is sleeping) of each day. When these stored autonomic parameters are plotted over time, the result is daytime trend 182 and nighttime trend 184. The difference between daytime trend 182 and nighttime trend 184 indicates that the autonomic tone of patient 14 remains healthy. Since autonomic tone manages thoracic fluid content, little to no difference between awake and sleep intrathoracic impedance measurements may suggest that autonomic tone is diminished. In addition, the increase of both daytime trend 182 and nighttime trend 184 over months 4 and 5 may suggest that the ANS health of patient 14 has been generally decreasing.

In other examples, the difference between daytime variability and nighttime variability may be directly calculated and plotted. Therefore, the graph may show the actual calculated difference between daytime and nighttime thoracic impedance variability. In the case of daytime trend 182 and daytime trend 184, this difference line may be generally flat as there is no change in the difference over time. However, a declining difference between daytime and nighttime measurements may be observed, and an appropriate treatment for patient 14 could be developed.

Further, the autonomic parameter used to generate graph 180 and illustrate the difference between day and night thoracic impedances may differ. For example, the autonomic parameter may be a variance, standard deviation, or standard error of the mean graph 180 may be presented on user interface 102 of programmer 24, on an external computing device 120 attached to network 112 of FIG. 6, a home patient module, or any other display mechanism.

Figure 10:
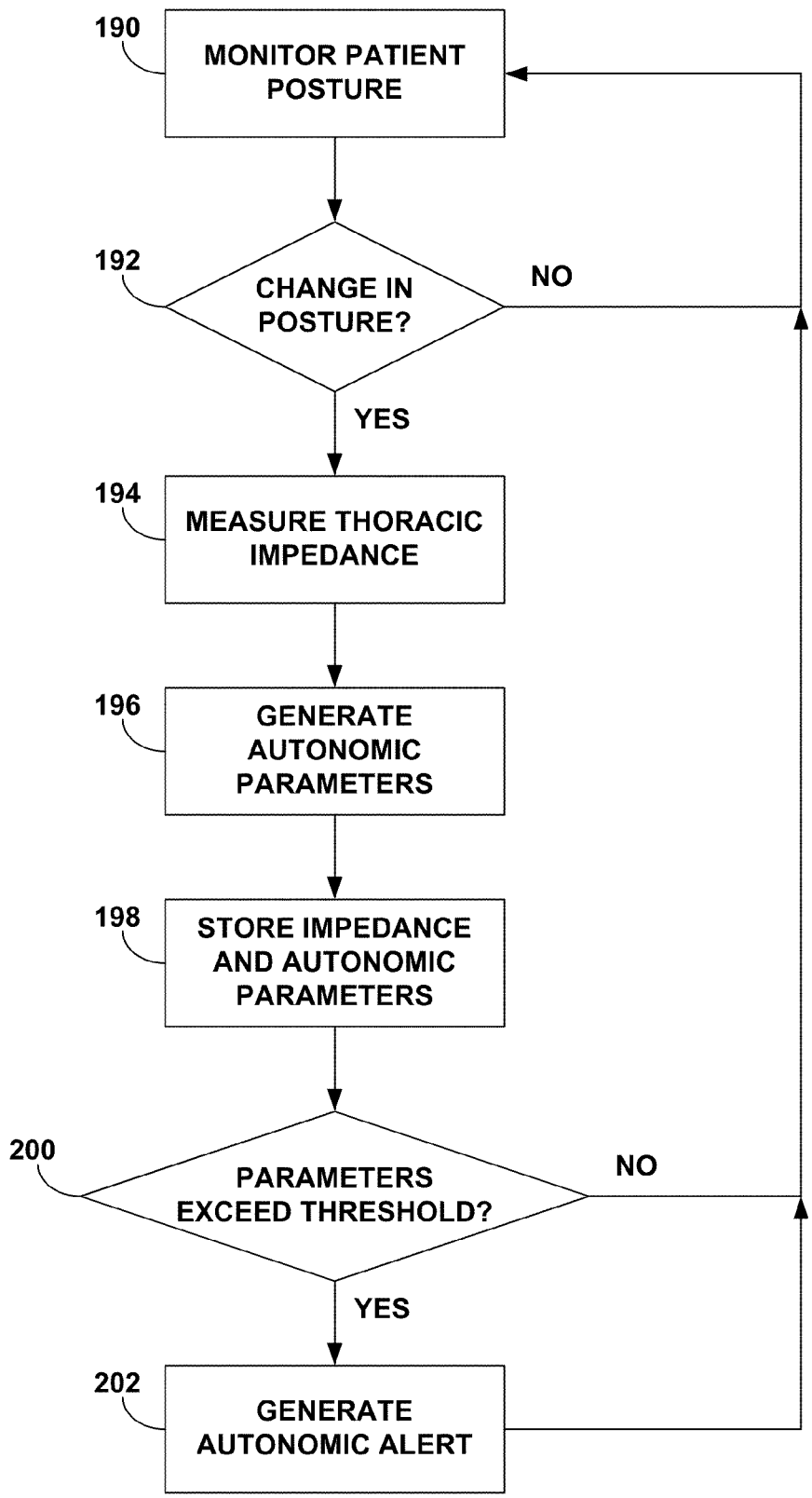
FIG. 10 is a flow diagram of an example method of measuring impedance in response to a change in patient posture.

FIG. 10 is a flow diagram of an example method of measuring impedance in response to a change in patient 14 posture. Although described as being performed by IMD 16 and processor 80, the example method may be performed by any device or processor, or combination of devices or processors, described herein.

As shown in FIG. 10, IMD 16 is engaged in acute monitoring of autonomic tone of patient 14. Processor 80 of IMD 16 continually monitors patient posture via posture module 89 (190). Posture module 89 may detect posture at any predetermined frequency. If processor 80 identifies a change in posture (192), processor 80 proceeds to measure the thoracic impedance of patient 14 (194). If there is no change in posture (192), then processor 80 continues to monitor posture (190). A change in posture may be identified when the signal from posture module 89 exceeds a predetermined threshold.

In some examples, processor 80 initiates impedance measurements, e.g., via signal generator 84 and sensing module 86, upon identification of the change in posture. In other examples, processor 80 continuously or periodically measures impedance, and selects measured impedances proximate in time to the change in posture, e.g., before and after, for analysis. In such examples, memory 82 may comprise a buffer for measured impedances.

Once processor 80 measures the thoracic impedance (194), processor 80 generates one or more autonomic parameters based upon the measured impedance and at least one previously measured thoracic impedance (196). For example, processor 80 may determine the amplitude or magnitude between a maximum and minimum of impedance measured proximate to the posture change (e.g., as illustrated in FIG. 7B) as an autonomic parameter. In other examples, processor 80 may additionally or alternatively determine other values representing the variability of the impedance values proximate the posture change, e.g., statistical measures of variability, such as variability, variance, standard deviation, range, or mean difference. Processor 80 determines which autonomic parameters to generate based upon instructions set by the user and stored in memory 82.

Processor 80 next stores the impedance measurement and generated autonomic parameters in memory 82 for later use and review (198). In some examples, values of the autonomic parameter may be available for viewing in the form of a trend diagram, histogram, or the like. Processor 80 continues to monitor posture (190) if none of the parameters exceed a threshold (200). However, if one of the autonomic parameters exceeds a threshold for the parameter (200), processor 80 generates an autonomic alert that is transmitted to the user indicating the exceeded autonomic parameter (202). An autonomic parameter exceeds a threshold if the parameter is less than a minimum value, more than a maximum value, or greater than an allowed variation from a threshold. The threshold may be a predetermined value, e.g., selected by a user, a baseline value, e.g., determined based on one or more baseline measurements of the patient's thoracic impedance, or an average of a number of previous measurements.

In some examples, the threshold that processor 80 compares the newly generated autonomic parameter against may be specific to a particular posture change type. Processor 80 may identify the posture change type detected by posture module 89 and compare the resulting autonomic parameters to previously generated autonomic parameters for only the same posture change type. In this manner, autonomic tone is always monitored in the same situation to prevent false negatives and false positives during diagnosis.

In other examples, the method of FIG. 10 may be applied to measure thoracic impedance in response to events other than or in addition to postures changes. For example, processor 80 may identify changes in activity, heart rate, temperature, or breathing rates or depth, the occurrence of neurological signal or event, gastrological signal or event, a tachyarrhythmia, or a premature ventricular complex, changes in a cardiac or cardiovascular pressure, or any other physiological attribute or event, and obtain and/or store a thoracic impedance measurement in response to the identified attribute or event in the same manner described herein with respect to posture or posture changes. In some examples, IMD 16 may include other sensors to detect such physiological events or attributes, such as pressure sensors or oxygen saturation sensors. Any detected changes in thoracic impedance over time, or temporal changes, may be used by processor 80 to determine ANS health or other baro-reflex sensitivity.

Figure 11:
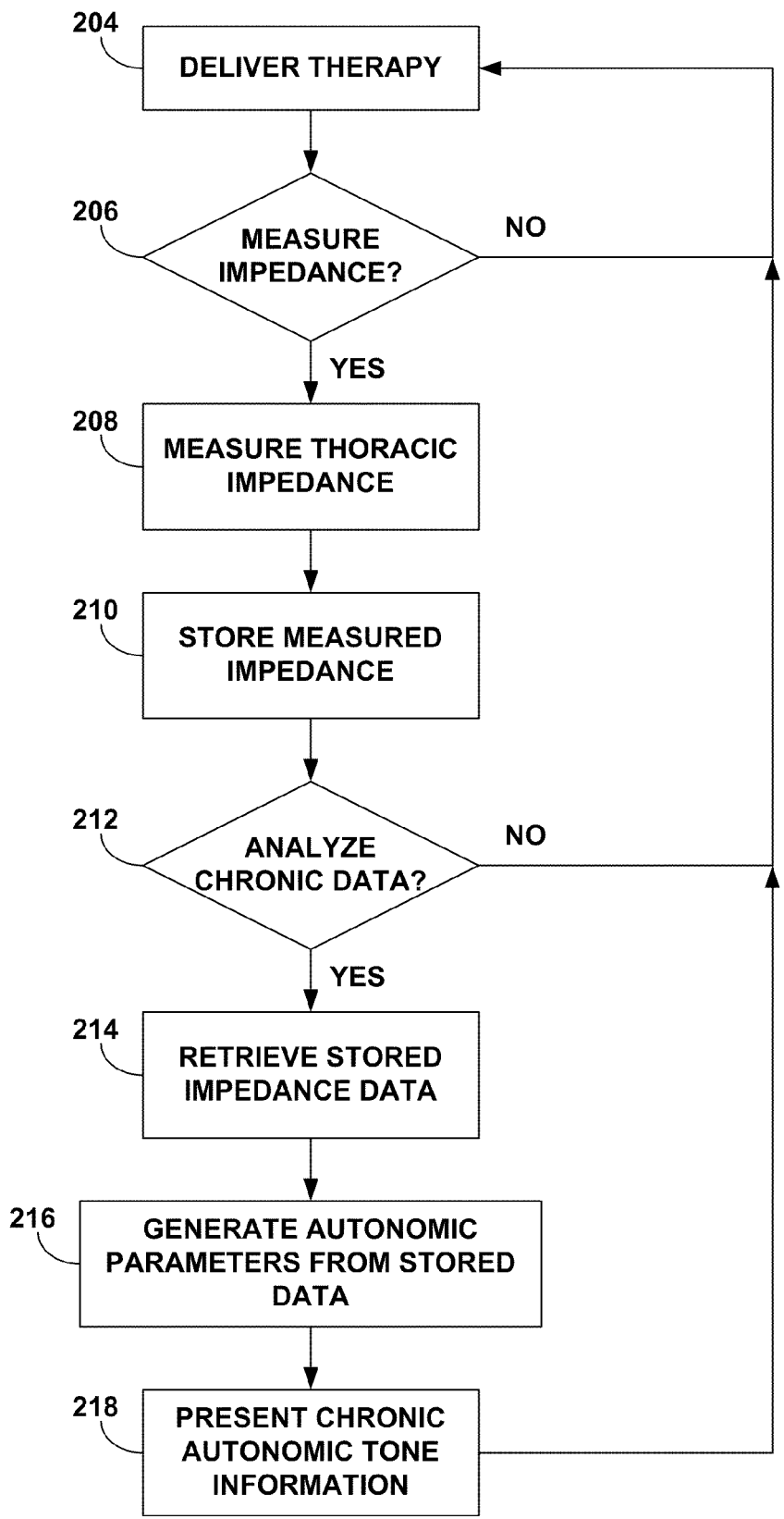
FIG. 11 is a flow diagram of an example method of chronic thoracic impedance monitoring.

FIG. 11 is a flow diagram of an example method of chronic intrathoracic impedance monitoring. Although described as being performed by IMD 16 and processor 80, the example method may be performed by any device or processor, or combination of devices or processors, described herein.

In the illustrated example, IMD 16 continually delivers therapy according to instructions stored in memory 82 (204). However, in some examples therapy may not be delivered when measuring thoracic impedance, or at all. If processor 80 determines that thoracic impedance should be measured (206), e.g., a timed schedule indicates that a measurement needs to be obtained, processor 80 measures the thoracic impedance of patient 14 (208). Processor 80 may control the measurement of impedance several times a day, an hour, a minute, or the like. Once the thoracic impedance is measured, processor 80 stores the measured impedance in memory 82 for later retrieval and analysis. If stored impedances do not need to be analyzed (212), the processor 80 continues to deliver therapy (204).

If the stored chronic data needs to be analyzed (212), processor 80 retrieves the stored impedance data from memory 82 (214). Processor 80 then generates autonomic parameters from the stored thoracic impedances so that the user can review the autonomic tone of patient 14 (216). For example, processor 80 may generate any of a variety of the variability values discussed above, e.g., daily values based on impedance measurements during a day. Processor 80 then transmits the autonomic parameters to an external computing device, e.g., programmer 24, so that the computing device can present the autonomic parameters as chronic autonomic tone information (218). The autonomic tone information may be presented in many different configurations according to the desires of the user, e.g., as a trend diagram of autonomic parameter values, e.g., a trend of daily thoracic impedance variability values. Processor 80 then continues to deliver therapy (204).

In alternative examples, all analysis of chronic thoracic impedances may be performed outside of IMD 16. Processor 80 may immediately transmit the stored impedances to the external computing device if the autonomic tone of patient 14 needs to be analyzed and reviewed (212). Every other analysis step and presentation step is then performed at the external computing device or some other device used to review patient 14 autonomic tone. On the other hand, processor 80 may automatically review the presented chronic autonomic tone information and predetermined times and only transmit an alert to the user if the information suggests a decline in autonomic tone.

Figure 12:
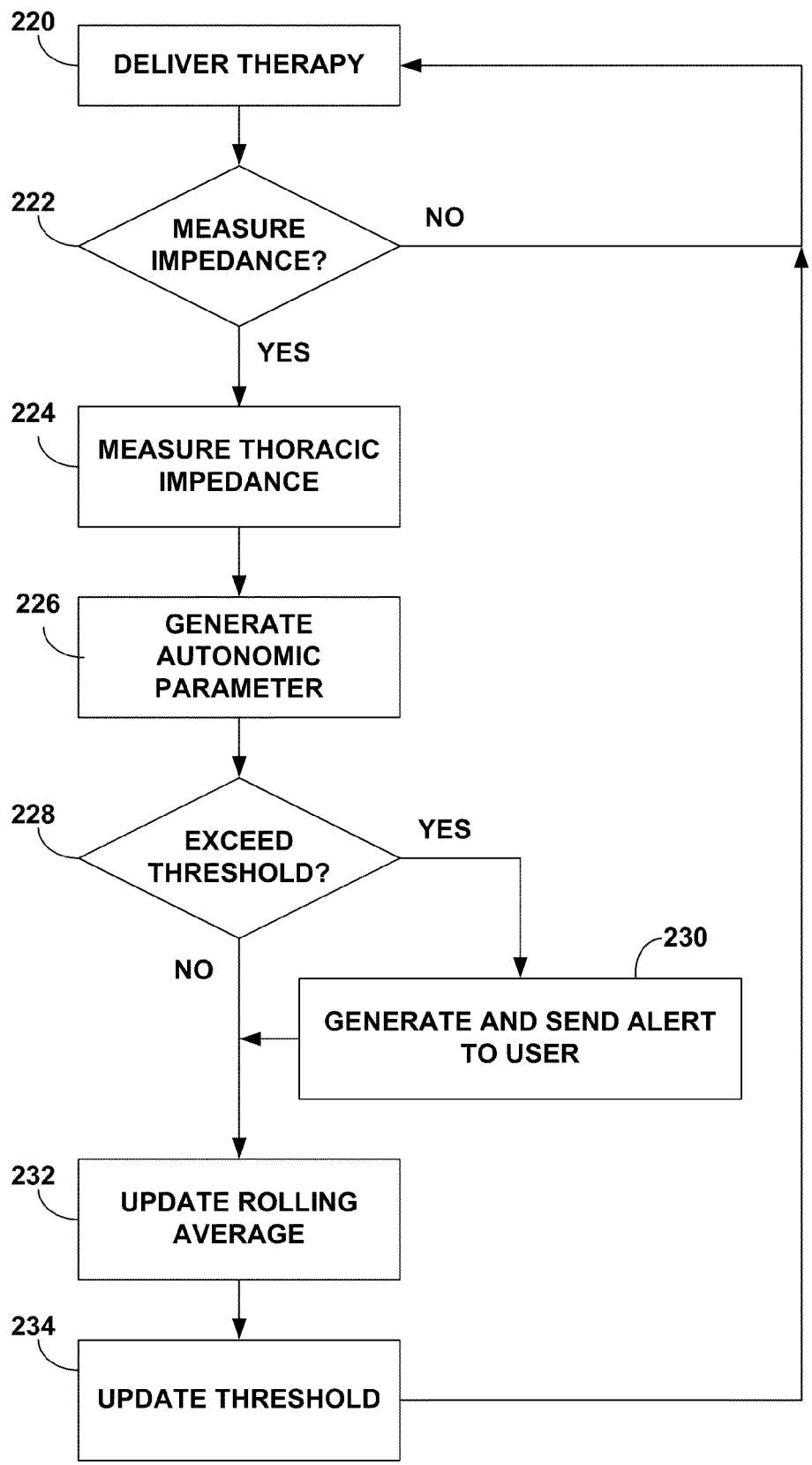
FIG. 12 is a flow diagram of an example method of monitoring autonomic tone with a rolling average of autonomic parameter values.

FIG. 12 is a flow diagram of an example method of monitoring autonomic tone with a rolling average of autonomic parameter values. Although described as being performed by IMD 16 and processor 80, the example method may be performed by any device or processor, or combination of devices or processors, described herein.

IMD 16 continually delivers therapy, e.g., atrial pacing, to patient 14 according to instructions stored in memory 82 (220). However, in some examples therapy may not be delivered when measuring thoracic impedance. If processor 80 determines that thoracic impedance should be measured (222), e.g., a timed schedule indicates that a measurement needs to be obtained, processor 80 measures the thoracic impedance of patient 14 (224). Processor 80 continues to deliver therapy if thoracic impedance does not need to be measured (220).

Processor then determines an autonomic parameter value, e.g., variability of thoracic impedance (226), and compares the measured impedance value to a threshold value determined based on the rolling average of autonomic parameter values stored in memory 82 (228). If the new impedance value exceeds the threshold or variation from the rolling average, processor 80 generates and sends an alert to the user identifying the change in autonomic tone (230). Furthermore, processor 80 updates the rolling average based on the new autonomic parameter value (232), and updates the threshold value based on the rolling average (234). The threshold may be the rolling average, or value determined based thereon, e.g., a ratio or percentage of the rolling average. Processor 80 then continues to deliver therapy to patient 14 (220).

Various examples have been described. These and other examples are within the scope of the following claims. For example, although the measurement of intrathoracic impedance for ANS monitoring is directed herein toward cardiac therapy, this disclosure may also be applicable to other therapies in which ANS health may be important. These therapies may include spinal cord stimulation, deep brain stimulation, pelvic floor stimulation, gastric stimulation, occipital stimulation, functional electrical stimulation, and any other stimulation therapy utilizing electrode sensing and/or stimulation methods. Furthermore, although described herein as implemented by an IMD and system including an IMD, in other examples, the techniques described herein may be implemented in an external pulse generator. An external pulse generator may be coupled to leads during implant and perform intrathoracic impedance measurements to quantify autonomic tone.

In addition, it should be noted that therapy system 10 may not be limited to treatment of a human patient. In alternative examples, therapy system 10 may be implemented in non-human patients, e.g., primates, canines, equines, pigs, and felines. These other animals may undergo clinical or research therapies that my benefit from the subject matter of this disclosure.

The techniques described in this disclosure, including those attributed to IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

The invention claimed is:

1. A method comprising:
    detecting a posture change of a patient;
    in response to detecting the posture change, obtaining a plurality of thoracic impedance values of the patient via a plurality of electrodes, wherein the plurality of impedance values are obtained during a period of time during which a variation of the plurality of impedance value is a result of the posture change; and
    generating a value of at least one autonomic parameter based on the variation of the plurality of thoracic impedance values that are a result of the posture change, the autonomic parameter value indicative of a relative autonomic nervous system (ANS) health of the patient,
    wherein greater variation of the plurality of impedance values that are a result of the posture change indicates greater ANS health.

2. The method of claim 1, wherein the at least one autonomic parameter value comprises at least one of an amplitude change of the impedance values, a difference between the impedance values, a variability of the impedance values, a variance of the impedance values, a standard deviation of the impedance values, a mean difference of the impedance values, or a standard error of the impedance values.

3. The method of claim 1, further comprising:
    comparing the value of the autonomic parameter to at least one earlier value of the autonomic parameter; and
    identifying the ANS health of the patient as one of declining, improving, or steady based upon the comparison.

4. The method of claim 1, further comprising detecting a physiological event of the patient, wherein obtaining the thoracic impedance values comprises measuring the thoracic impedance values in response to detecting the physiological event.

5. The method of claim 1, wherein the first posture change comprises one of standing up, sitting up, sitting down, reclining back, laying down, starting to exercise, or stopping exercise.

6. The method of claim 1, wherein obtaining the plurality of thoracic impedance values comprises measuring the plurality of thoracic impedance values with an implanted medical device.

7. The method of claim 6, wherein generating the value of the at least one autonomic parameter comprises generating the value by the implanted medical device.

8. The method of claim 6, further comprising storing at least one of the thoracic impedance values and the generated autonomic parameter value in a memory of an implanted medical device.

9. The method of claim 8, further comprising transmitting at least one of the stored thoracic impedance values or the stored autonomic parameter value from the implanted medical device to an external computing device.

10. The method of claim 9, further comprising presenting a plurality of values of the autonomic parameter in at least one of a graphical or numerical format on the external computing device.

11. The method of claim 10, further comprising presenting a trend of the values of the autonomic parameter.

12. A system comprising:
    a posture module configured to detect a posture change of a patient;
    a plurality of electrodes;
    a sensing module configured to, in response to detection of the posture change by the posture module, obtain a plurality of thoracic impedance values of the patient via the electrodes, wherein the plurality of impedance values are obtained during a period of time during which a variation of the plurality of impedance value is a result of the posture change; and
    a processor configured to generate a value of at least one autonomic parameter based on the variation of the plurality of thoracic impedance values that are a result of the posture change, the autonomic parameter value indicative of a relative autonomic nervous system (ANS) health of the patient,
    wherein greater variation of the plurality of impedance values that are a result of the posture change indicates greater ANS heath.

13. The system of claim 12, wherein the at least one autonomic parameter value comprises at least one of an amplitude change of the impedance values, a difference between the impedance values, a variability of the impedance values, a variance of the impedance values, a standard deviation of the impedance values, a mean difference of the impedance values, or a standard error of the impedance values.

14. The system of claim 12, further comprising an implantable medical device coupled to the electrodes, wherein the implantable medical device comprises the sensing module.

15. The system of claim 14, wherein the implantable medical device comprises the processor.

16. The system of claim 14, further comprising an external computing device, wherein the implantable medical device is configured to transmit at least one of the thoracic impedance values or the autonomic parameter value to the external computing device.

17. The system of claim 16, wherein the external computing device is configured to present a plurality of values of the autonomic parameter in at least one of a graphical or numerical format.

18. The system of claim 17, wherein the external computing device is configured to present a trend of the values of the autonomic parameter.

19. A system comprising:
    means for detecting a posture change of a patient;
    means for, in response to detecting the posture change, obtaining a plurality of thoracic impedance values of the patient via a plurality of electrodes, wherein the plurality of impedance values are obtained during a period of time during which a variation of the plurality of impedance value is a result of the posture change; and
    means for generating a value of at least one autonomic parameter based on the variation of the plurality of thoracic impedance values that are a result of the posture change, the autonomic parameter value indicative of a relative autonomic nervous system (ANS) health of the patient, wherein greater variation of the plurality of impedance values that are a result of the posture change indicates greater ANS health.

20. A computer-readable storage medium comprising instructions that cause a processor to:

detect a posture change of a patient;

in response to detecting the posture change, obtain a plurality of thoracic impedance values of the patient via a plurality of electrodes, wherein the plurality of impedance values are obtained during a period of time during which a variation of the plurality of impedance value is a result of the posture change; and generate a value of at least one autonomic parameter based on the variation of the thoracic impedance values that are a result of the posture change, the autonomic parameter value indicative of a relative autonomic nervous system (ANS) health of the patient, wherein greater variation of the plurality of impedance values that are a result of the posture change indicates greater ANS health.

* * * * *